US010532166B2

(12) United States Patent
Schriver et al.

(10) Patent No.: US 10,532,166 B2
(45) Date of Patent: Jan. 14, 2020

(54) SYSTEM AND METHOD FOR IDENTIFYING A FILL VOLUME OF A FLUID CHAMBER

(71) Applicant: BAYER HEALTHCARE LLC, Whippany, NJ (US)

(72) Inventors: Ralph Schriver, Tarentum, PA (US); Arthur E Uber, III, Pittsburgh, PA (US); Michael Spohn, Fenelton, PA (US)

(73) Assignee: BAYER HEATLHCARE LLC, Whippany, NJ (US)

( * ) Notice: Subject to any disclaimer, the term of this patent is extended or adjusted under 35 U.S.C. 154(b) by 201 days.

(21) Appl. No.: 15/643,542

(22) Filed: Jul. 7, 2017

(65) Prior Publication Data
US 2018/0008787 A1  Jan. 11, 2018

Related U.S. Application Data

(60) Provisional application No. 62/421,692, filed on Nov. 14, 2016, provisional application No. 62/359,911, filed on Jul. 8, 2016.

(51) Int. Cl.
*A61M 5/36* (2006.01)
*A61M 5/145* (2006.01)
(Continued)

(52) U.S. Cl.
CPC .......... *A61M 5/365* (2013.01); *A61M 5/142* (2013.01); *A61M 5/1456* (2013.01);
(Continued)

(58) Field of Classification Search
CPC .. A61M 2205/3306; A61M 2205/3389; A61M 5/007; A61M 5/1411
See application file for complete search history.

(56) References Cited

U.S. PATENT DOCUMENTS

| | | | |
|---|---|---|---|
| 3,597,973 A | | 8/1971 | Francis |
| 4,345,483 A | * | 8/1982 | Paletta ................. A61M 5/172 422/562 |

(Continued)

FOREIGN PATENT DOCUMENTS

| | | |
|---|---|---|
| DE | 4319115 A1 | 12/1994 |
| EP | 2327431 A1 | 6/2011 |

(Continued)

OTHER PUBLICATIONS

"Extended Uropean Search Report from EP Application No. 17180202", dated Nov. 16, 2017.

(Continued)

*Primary Examiner* — Laura A Bouchelle
(74) *Attorney, Agent, or Firm* — David Schramm; Joseph L. Kent; James R. Stevenson

(57) ABSTRACT

A system and method for determining the fill volume of a fluid chamber includes a fluid injector, at least one fluid chamber in fluid communication with the fluid injector, one or more sensors positioned relative to the at least one fluid chamber and configured to detect a position of a liquid-gas interface of the fluid contained in the at least one fluid chamber, and at least one processor in communication with the sensors and the fluid injector, and configured to: determine the position of the liquid-gas interface of the fluid, calculate the volume of fluid in the at least one fluid chamber based on the position of the liquid-gas interface, and at least one of: i) display the volume of the fluid; ii) enable the fluid injector to perform an action; and iii) disable the fluid injector from performing the action.

20 Claims, 14 Drawing Sheets

(51) Int. Cl.
*A61M 5/142* (2006.01)
*A61M 5/20* (2006.01)
*A61M 5/00* (2006.01)
*A61M 5/14* (2006.01)
*A61M 5/178* (2006.01)

(52) U.S. Cl.
CPC .......... *A61M 5/204* (2013.01); *A61M 5/2066* (2013.01); *A61M 5/007* (2013.01); *A61M 5/1407* (2013.01); *A61M 2005/1404* (2013.01); *A61M 2005/1787* (2013.01)

(56) References Cited

U.S. PATENT DOCUMENTS

| | | |
|---|---|---|
| 4,384,581 A | 5/1983 | Conway |
| 4,452,251 A | 6/1984 | Heilman |
| 4,854,324 A | 8/1989 | Hirschman et al. |
| 5,254,101 A | 10/1993 | Trombley, III |
| 5,383,858 A | 1/1995 | Reilly et al. |
| 5,807,321 A | 9/1998 | Stoker et al. |
| 5,858,239 A * | 1/1999 | Kenley ............... A61M 1/3627 210/646 |
| 5,873,861 A | 2/1999 | Hitchins et al. |
| 6,322,535 B1 | 11/2001 | Hitchins et al. |
| 6,626,862 B1 | 9/2003 | Duchon et al. |
| 6,652,489 B2 | 11/2003 | Trocki et al. |
| 7,094,216 B2 | 8/2006 | Trombley et al. |
| 7,553,294 B2 | 6/2009 | Lazzaro et al. |
| 7,556,619 B2 * | 7/2009 | Spohn ............... A61G 7/0503 604/251 |
| 7,666,169 B2 | 2/2010 | Cowan et al. |
| 7,753,885 B2 | 7/2010 | Duchon et al. |
| 7,937,134 B2 | 5/2011 | Uber, III |
| 8,147,464 B2 | 4/2012 | Spohn et al. |
| 8,173,995 B2 | 5/2012 | Ramakrishnan et al. |
| 8,337,456 B2 | 12/2012 | Schriver et al. |
| 8,403,909 B2 | 3/2013 | Spohn et al. |
| 8,506,523 B2 | 8/2013 | Miyazaki et al. |
| 8,882,704 B2 | 11/2014 | Fago et al. |
| 9,082,157 B2 | 7/2015 | Gibson |
| 9,173,995 B1 | 11/2015 | Tucker et al. |
| 9,199,033 B1 | 12/2015 | Cowan et al. |
| 9,250,111 B2 | 2/2016 | Whalley et al. |
| 9,259,526 B2 | 2/2016 | Barron et al. |
| 9,474,857 B2 | 10/2016 | Riley et al. |
| 2008/0086087 A1 | 4/2008 | Spohn et al. |
| 2008/0167615 A1 | 7/2008 | Niehoff |
| 2008/0306443 A1 | 12/2008 | Neer et al. |
| 2009/0188311 A1 | 7/2009 | Cadieux et al. |
| 2011/0056290 A1 | 3/2011 | Bryant et al. |
| 2011/0208350 A1 | 8/2011 | Eliuk et al. |
| 2012/0127290 A1 | 5/2012 | Tojo et al. |
| 2013/0150821 A1 | 6/2013 | Bollish et al. |
| 2013/0310756 A1 | 11/2013 | Whalley et al. |
| 2014/0027009 A1 | 1/2014 | Riley et al. |
| 2014/0045668 A1 * | 2/2014 | Case ................ A61M 1/3696 494/1 |
| 2014/0088494 A1 | 3/2014 | Shearer, Jr. et al. |
| 2015/0003741 A1 | 1/2015 | Zhang et al. |
| 2015/0125945 A1 | 5/2015 | Holmes et al. |
| 2016/0030673 A1 | 2/2016 | White et al. |
| 2016/0296692 A1 | 10/2016 | Agris, III et al. |
| 2017/0035974 A1 | 2/2017 | Berry et al. |
| 2017/0056603 A1 | 3/2017 | Cowan et al. |
| 2017/0319809 A1 * | 11/2017 | Biba ................ A61M 16/1005 |

FOREIGN PATENT DOCUMENTS

| | | |
|---|---|---|
| WO | 2007064234 A1 | 6/2007 |
| WO | 2008051576 A2 | 5/2008 |
| WO | 2009025996 A1 | 2/2009 |
| WO | 2012155035 A1 | 11/2012 |
| WO | 2014160307 A1 | 10/2014 |
| WO | 2015081109 A1 | 6/2015 |
| WO | 2015116637 A2 | 8/2015 |
| WO | 2015164783 A1 | 10/2015 |
| WO | 2016069711 A1 | 5/2016 |
| WO | 2016069714 A1 | 5/2016 |
| WO | 2016112163 A1 | 7/2016 |
| WO | 2016172467 A1 | 10/2016 |
| WO | 2016191485 A1 | 12/2016 |

OTHER PUBLICATIONS

Comar., "Oral Syringes", Jul. 2015.
"International Preliminary Report on Patentability from PCT Application No. PCT/US2015/034873", dated Dec. 22, 2016.
"International Search Report and Written Opinion from corresponding PCT App. No. PCT/US2016/048441", dated Dec. 7, 2016.
"International Search Report from PCT/US2015/034873", dated Sep. 4, 2015.
Mallinckrodt; Pharmaceuticals., "Power Injectors for Diagnostic Imaging", 2013.
Sidam; Medical Devices., "Injector Syringe With Automatic Three-Way Valve (received Jul. 9, 2014)".
"Extended European Search Report from EP App. No. 16842618", dated Mar. 7, 2019.

* cited by examiner

SYSTEM AND METHOD FOR IDENTIFYING A FILL VOLUME OF A FLUID CHAMBER

CROSS REFERENCE TO RELATED APPLICATIONS

This application claims priority to U.S. Provisional Patent Application Ser. Nos. 62/421,692, entitled "Optical Detection of a Liquid-Gas Interface in a Drip Chamber", filed Nov. 14, 2016, and 62/359,911, entitled "Display for Identifying a Fill Volume of a Fluid Container", filed Jul. 8, 2016. The contents of each of these applications are incorporated herein by reference. This application also incorporates by reference U.S. patent application Ser. No. 15/249,667, filed on Aug. 29, 2016, and published as U.S. Patent Application Publication No. 2017/0056603.

BACKGROUND OF THE DISCLOSURE

Field of the Disclosure

The present disclosure relates generally to a system for determining the amount of fluid remaining in a fluid chamber to be injected into a patient by a syringe and/or other fluid injector, a method for the same, and a display for the same. In other aspects, the present disclosure relates to systems and methods for identifying the various features and properties of the fluid within the syringe or other fluid chamber.

Description of Related Art

In many medical diagnostic and therapeutic procedures, a medical practitioner, such as a physician, nurse, or medical technician, injects a patient with one or more medical fluids. In recent years, a number of injector-actuated syringes and fluid injectors for pressurized injection of fluids, such as a contrast imaging agent solution (often referred to as "contrast"), a flushing agent, such as saline, and other medical fluids have been developed for use in procedures such as angiography, computed tomography ("CT"), ultrasound, magnetic resonance imaging ("MRI"), nuclear medicine, positron emission tomography ("PET"), and other imaging procedures. In general, these fluid injectors are designed to deliver a preset amount of fluid at a preset flow rate.

In some injection procedures, the medical practitioner places a catheter or a needle connected to tubing, or other fluid delivery connection into a vein or artery of the patient. The catheter or the tubing is connected to either a manual or a powered automatic fluid injection mechanism. Automatic fluid injection mechanisms typically include a connector to a fluid injector having, for example, at least one powered linear piston and/or a peristaltic pump. The syringe may include a source of contrast and/or a source of flushing fluid. The medical practitioner enters settings into an electronic control system of the fluid injector for a fixed volume of contrast and/or saline, a fixed rate of injection for each, and specific times for injections of each of the one or more fluids.

The injected contrast and/or saline are delivered to a patient's vasculature through the catheter or needle inserted into the patient's body, such as the patient's arm or groin area. A dose of contrast is referred to as a bolus. Once the bolus of contrast is delivered to the desired site, that area is imaged using a conventional imaging technique, such as angiography imaging or scanning, CT, ultrasound, MRI, PET, and/or other imaging procedures. The presence of the contrast becomes clearly visible against the background of the surrounding tissue.

Conventional injector design includes a controller, including soft buttons and readouts, located on the face of the injector assembly which requires the user or technician to enter injection data, such as the volume of fluids to be injected into a patient, and monitor the injection while remaining within arms-length of the injector assembly. An injection procedure cannot properly be completed when the supply of a fluid to be injected becomes exhausted before the procedure is completed. Thus, it is important for a user to track the volume of fluid that is in fluid communication with the injector in order to ensure that the supply of a fluid to be injected remains available during the injection procedure. One known system and method for doing so involves a user of a fluid injector manually entering a volume of a fluid or fluids into the controller or another computer. The processor of the controller or other computer includes software that tracks the amount of fluid or fluids injected into a patient, and a computer processor calculates the volume of fluid or fluids remaining over time based on an initial volume entered by the user. The calculated remaining volumes of contrast, saline, and/or other fluid to be injected may be displayed on a graphical user interface ("GUI") for the benefit of the user. Another known system is for the injector to know the volume of fluid in its syringes based on the plunger position in the syringe, assuming that the user has properly filled and confirmed that the syringes are full of the proper fluid.

However, the above systems and methods may be vulnerable to user error. For example, a user may inadvertently enter an incorrect value of the volume of fluid or fluids in fluid communication with the injector. This may occur, for example, due to mislabeling of a fluid container, or by simply inadvertently pressing the wrong button.

In addition, since most medical fluids used with power injectors are clear or only slightly tinted, and it may be difficult for a technician to quickly and easily distinguish when fluid is present in a translucent syringe or other fluid chamber. Accordingly, a need exists for a system used with a fluid injection device that is capable of differentiating between air and different types of fluid. In addition, automated systems that can determine various properties of the fluid, for example by analyzing properties and/or changes of the interaction between electromagnetic radiation with the contents of the fluid chamber, and communicating those properties to the user, for example via a display screen, are also desirable.

Moreover, it is a concern that user error in entering the correct volume of fluid contained in a fluid chamber may result in a lack of synchronization between the calculated volume of fluid in a fluid chamber, and an actual volume. This lack of synchronization may result in a power injector system failing to complete an injection procedure, as the injector system is unable to confirm that adequate medical fluid exists to complete an injection protocol. This is of particular concern for power injectors which include peristaltic pumps or other direct infusion injector systems, and may result in unnecessary diagnostic scans and repeat scans, which in turn leads to an unnecessary waste of fluid and/or wasted radiation dose to the patient.

Thus, a need exists for a system and method to accurately track the volume of fluid available to be injected into a patient during an injection procedure.

SUMMARY OF DISCLOSURE

Accordingly, it is an object of the present disclosure to provide a system and method for monitoring the remaining volume of fluid or fluids in communication with a fluid injector that overcomes various deficiencies in the prior art.

In a non-limiting example of the present disclosure, a system for delivering fluid to a patient may comprise an injector housing comprising at least one syringe port adapted to releasably engage at least one syringe; and a fluid control device adapted to interface with the injector and actuate at least one syringe engaged in the at least one syringe port, the fluid control device comprising at least one processor programmed or configured to control a fluid delivery. The fluid control device may comprise or connect to a user interface, which may comprise a graphical user interface ("GUI"). In another non-limiting example, the fluid injector may further comprise an additional injection fluid or fluids, such as second and/or third injection fluids that may be mixed with the first injection fluid prior to being delivered to a patient or delivered directly to the patient without mixing, depending on the mode of operation of the injector. The second and/or third fluids may be advanced by a pumping mechanism such as a peristaltic pump or a syringe pump. In some examples, the second and/or third fluids may be advanced to, from, and/or through drip chambers, as described herein. Non-limiting examples of second and/or third fluids are medical fluids, such as saline or contrast media.

In non-limiting examples, fill volume of a fluid or fluids to be injected may be monitored by at least one sensor, including, without limitation, an optical sensor, such as a camera, cameras, charge coupled devices (CCDs), photosensitive detectors, and/or ultrasonic devices measuring levels of fluid within the containers. A single sensor may be used, or the sensors may be positioned in one or more arrays. In further examples according to the present disclosure, fill volume may be monitored by taking measurements of the mass (or weight) of the containers and the fluid contained therein. Data from the fill volume measurements may be sent to the fluid control device which may be in wired or wireless communication with the at least one sensor. These data, along with data regarding the amount of fluid injected over time by the fluid injector, may be used to calculate the volume or amount of the fluid remaining in the fluid chamber without manual input of fill volume data by a user into the fluid control device. The calculated value of the volume or amount may then be displayed on the GUI, either numerically or graphically. In a non-limiting example according to the present disclosure, a processor may alert the user, allow, or prohibit the injector from performing an action based on the determined volume of the fluid in the fluid chamber or fluid chambers.

In a further example, standardized containers of known mass and/or volume may be used to contain fluid. The fluid containers may be labeled with fill information in an electronically-readable medium, such as, without limitation, magnetic tape, a magnetic tag, an RF-ID label, a bar code, a label such as a barcode or QR code, or other indicator which provides information. When read by the sensor, these data are transmitted to the fluid control device. These data may be used to calculate the fluid volume remaining on the container. Along with data regarding the amount of volume injected into a patient over time, the data allows the fluid control device to calculate and track the fill volume of a container or containers without manual input of volume data by a user into the fluid control device.

In certain examples according to the present disclosure, the fluid control device may electronically communicate with a user interface with a display and/or a GUI. Non-limiting examples of a user interface include at least a computer such as a desktop computer, a laptop computer, tablet computer, smartphone or personal data assistant device, or other handheld or otherwise portable computer processor. The at least one computer may be programmed or configured to be in wireless and, optionally, wired electronic communication with the at least one processor or injector system and to receive fill volume data, calculate fill volume, track a fill volume, and/or display a value of a fill volume. The fluid control device may be configured or programmed to execute at least one control option based at least partially on instructions received and/or delivered from the at least one portable computer.

In another example according to the present disclosure, a system for determining a position of a liquid-gas interface in a drip chamber of an injection device may comprise a fluid path set comprising at least one primary fluid container, a syringe, and an output line, at least a portion of or all of which may be in fluid communication with the drip chamber, wherein the primary fluid container is configured to deliver fluid to the drip chamber; and a fluid level sensing mechanism including at least one sensor configured to observe a position of the liquid-gas interface in the drip chamber, wherein the sensor returns data on or related to the position of the liquid-gas interface to a controlling mechanism. The system also may comprise a fluid level sensing mechanism including more than one sensor.

According to another non-limiting example, this disclosure relates to a system for determining a volume of fluid available to be injected into a patient, the system comprising a fluid injector housing adapted to releasably engage at least one syringe, at least one fluid container in fluid communication with the at least one syringe, a fluid control device adapted to interface with and actuate a fluid injector to operate the least one syringe, the fluid control device comprising at least one processor programmed or configured to control a fluid delivery of at least one fluid to the patient, at least one sensor configured to measure a volume of fluid in the at least one container and in electronic communication with the at least one processor, wherein the at least one sensor reads data on the volume or amount of fluid contained in the at least one container and communicates the data to the processor, and wherein the processor calculates a value of the volume or amount of fluid in the at least one container.

A non-limiting example according to the present disclosure, may further comprise a user interface in electronic communication with the processor and a user-readable display, wherein the processor may communicate the value of the volume or amount of fluid in the at least one container to the user interface, and wherein the display of the user interface displays the value.

According to a further non-limiting example, this disclosure relates to a method for calculating a volume of fluid available to be injected into a patient, the method comprising a fluid injector adapted to releasably engage at least one syringe, at least one fluid container in fluid communication with the at least one syringe, a fluid control device adapted to interface with and actuate the fluid injector to operate the at least one syringe, the fluid control device comprising at least one processor programmed or configured to control a fluid delivery of at least one fluid to at least one patient, and at least one sensor configured to detect a position of fluid in the at least one container, and in electronic communication with the at least one processor, reading a data on the volume or amount of fluid contained in the at least one container, communicating the data to the processor, and calculating a value of the volume or amount of fluid in the at least one fluid container.

A non-limiting example may further comprise communicating the value to a user interface in electronic communication with the processor, and displaying the value on a user-readable display of the user interface.

According to another non-limiting example, this disclosure relates to a system for determining a volume of fluid available to be injected into a patient, the system comprising a fluid injector adapted to releasably engage at least one syringe, a fluid control device adapted to interface with and actuate the fluid injector to operate the least one syringe, the fluid control device comprising at least one processor programmed or configured to control a fluid delivery of at least one fluid to the patient, at least one sensor configured to measure a volume of fluid in the at least one syringe and in electronic communication with the at least one processor, wherein the sensor reads a data on the volume or amount of fluid contained in the at least one syringe and communicates the data to the processor, and wherein the processor calculates a value of the volume or amount of fluid in the at least one syringe.

A non-limiting example may further comprise a user interface in electronic communication with the processor and a user-readable display, wherein the processor communicates the value of the volume or amount of fluid in the at least one syringe to the user interface, and wherein the display of the user interface displays the value.

In another non-limiting example, the present disclosure relates to a fluid injection system comprising a fluid injector; at least one fluid chamber configured to contain fluid, the at least one fluid chamber in fluid communication with the fluid injector; one or more sensors positioned relative to the at least one fluid chamber and configured to detect a position of a liquid-gas interface of the fluid contained in the at least one fluid chamber; and at least one processor in communication with the one or more sensors and the fluid injector, the at least one processor configured to determine the position of the liquid-gas interface of the fluid in the at least one fluid chamber; calculate the volume or amount of fluid contained in the at least one fluid chamber based on the position of the liquid-gas interface of the fluid in the at least one fluid chamber, and at least one of: i) display on a display in communication with the at least one processor the volume or amount of the fluid contained in the at least one fluid chamber; ii) enable the fluid injector to perform an action; and iii) disable the fluid injector from performing the action.

The fluid injection system may comprise at least one of contrast media container and a saline container. The fluid injection system may further comprise a fluid injector including a pump and which is in fluid communication with a fluid path set; wherein the at least one fluid chamber further includes at least one drip chamber in fluid communication with the fluid injector and at least one of the contrast media container and the saline container; and wherein at least one of the one or more sensors is positioned relative to the at least one drip chamber and configured to detect the position of a liquid-gas interface of a fluid contained in the at least one drip chamber. In non-limiting examples, the pump may include a peristaltic pump, a piston pump, or a syringe pump.

In examples according to the present disclosure, the display may comprise a GUI, wherein the position of the liquid-gas interface of the fluid in the at least one fluid chamber is displayed on the GUI.

In an example, the fluid injection system may comprise an actuator configured to actuate the one or more sensors wherein the one or more sensors are actuated to move in response to the position of the liquid-gas interface of the fluid in the at least one fluid chamber.

Examples of the present disclosure further relate to a method for determining the volume or amount of fluid in at least one fluid chamber of a fluid injection system comprising a fluid injector, comprising the steps of positioning one or more sensors relative to the at least one fluid chamber, wherein the one or more sensors are in communication with at least one processor in communication with the fluid injector; detecting with the one or more sensors a position of a liquid-gas interface of the fluid contained in the at least one fluid chamber; taking position data of the liquid-gas interface of the fluid contained in the at least one fluid chamber with at least one of the one or more sensors; determining the position of the liquid-gas interface of the fluid in the at least one fluid chamber from the position data; calculating the volume or amount of fluid contained in the at least one fluid chamber based on the position of the liquid-gas interface of the fluid in the at least one fluid chamber; and at least one of: i) displaying on a display in communication with the at least one processor the volume of the fluid contained in the at least one fluid chamber; ii) enabling the fluid injector to perform an action; iii) informing the user of insufficient volume and allowing the user to install a fluid container with sufficient fluid, iv) informing the user of insufficient volume and allowing the user to continue with an system or user adjusted volume; and v) disabling the fluid injector from performing the action.

The method may comprise a feature wherein one or more of the steps of enabling the fluid injector to perform the function, alerting the user, adjusting the volume, and/or disabling the fluid injector from performing the action, are automatically completed by the at least one processor.

The method may comprise the steps of determining the volume or amount of fluid contained in the at least one fluid chamber by comparing the position data with known positions corresponding to known volumes or amounts of fluid.

The method may comprise the steps of positioning a position measuring scale within a field of detection of the one or more sensors; comparing the position data with the positioning measuring scale; and determining the volume or amount of fluid contained in the at least one fluid chamber based on a relative position of the liquid-gas interface and a value indicated by the measuring scale.

In a non-limiting example, a fluid injection system is provided, comprising an injector assembly with at least one syringe port, a controller, and a wired or wirelessly connected user interface, such as an integrated computer or detachable portable computer, which may have a touch screen or other user input device, and/or a display configured for inputting one or more injection parameters and displaying one or more injection parameters or features, including without limitation a calculated remaining fill volume or amount of a fluid or fluids to be injected into a patient. Examples of suitable detachable computers may include, but are not limited to, a desktop computer, a laptop computer, a tablet computer, a smartphone or a personal data assistant device, or other handheld computer processor. The computer may be in communication with the controller by a wired or wireless communication mechanism.

In another non-limiting example according to the present disclosure, an injector system is provided that comprises a first drip chamber in fluid connection between the source of saline and a pump and a detector in operative connection with the first drip chamber to sense the amount of saline in the source of saline as part of a fluid path set. Likewise, embodiments of an injector system may comprise a second drip chamber in fluid connection between the source of contrast and the contrast valve and a detector in operative connection with the second drip chamber to sense the amount of injection fluid in the source of injection fluid. One advantage of a drip chamber is to reduce likelihood of introduction of air into the system once the system has been initially purged of air or primed. Conventional drip chamber detectors are configured to detect a presence or absence of fluid within the drip chamber, but not to detect a position of the liquid-gas interface within the drip chamber that is indicative of an overall fluid level in the associated primary fluid source.

An aspect of the present disclosure is directed to an improved drip chamber that may be used as part of the fluid path set. For example, one or more drip chambers may be used with the first section, or the second section of the fluid path. In an embodiment, the first section may include an intervening drip chamber between the primary fluid source and the syringe or other pump. In some embodiments, the drip chamber may comprise a projection useful for determining a level of fluid in the drip chamber. The projection may be raised from the body of the drip chamber, and may extend longitudinally or laterally along the body of the drip chamber. However, it is to be understood that the projection is not necessary to the embodiments according to the present disclosure.

The fluid path set may comprise a drip chamber and the fluid control device may include at least one fluid level sensing mechanism operatively associated with the drip chamber for sensing the injection fluid level in the drip chamber. The fluid level sensing mechanism may comprise an optical or ultrasonic apparatus, and may measure changes in liquid-gas interface levels in the drip chamber. Examples of fluid sensing mechanisms are described herein.

In one example, a system for determining a position of a liquid-gas interface in a drip chamber of an injection device comprises a fluid path set comprising at least one primary fluid container, a syringe, and an output line, at least a portion of or all of which are in fluid communication with the drip chamber, wherein the primary fluid container is configured to deliver fluid to the drip chamber; and a fluid level sensing mechanism including at least one sensor configured to detect a position of the liquid-gas interface in the drip chamber, wherein the sensor returns data on the position of the liquid-gas interface to a controller.

Non-limiting examples of fluid injection or delivery systems consistent with the disclosure herein are found in U.S. Pat. No. 7,094,216; U.S. Provisional Application Ser. No. 62/363,668; International Application Publication Nos. WO 2016/112163; WO 2016/172467; WO 2016/191485; WO 2017/040152; and International Application No. PCT/US2017/036941, the disclosures of each of which are incorporated herein by reference in their entirety. Additional examples of suitable fluid injectors are disclosed in the following references: U.S. Pat. Nos. 7,556,619; 8,337,456; 8,147,464; and U.S. Patent Application Publication No. 2008/0086087, the disclosures of each of which are incorporated herein by reference in their entirety.

While multiple examples of systems and methods for identifying a fill volume of a fluid chamber are shown in the accompanying Figures and described herein in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

BRIEF DESCRIPTION OF THE DRAWINGS

For the purpose of facilitating understanding of this disclosure, the accompanying drawings and description illustrate certain embodiments, from which the various discussed structures, construction, method of operation, and many advantages provided by this disclosure may be understood and appreciated.

DETAILED DESCRIPTION

Figure 1:
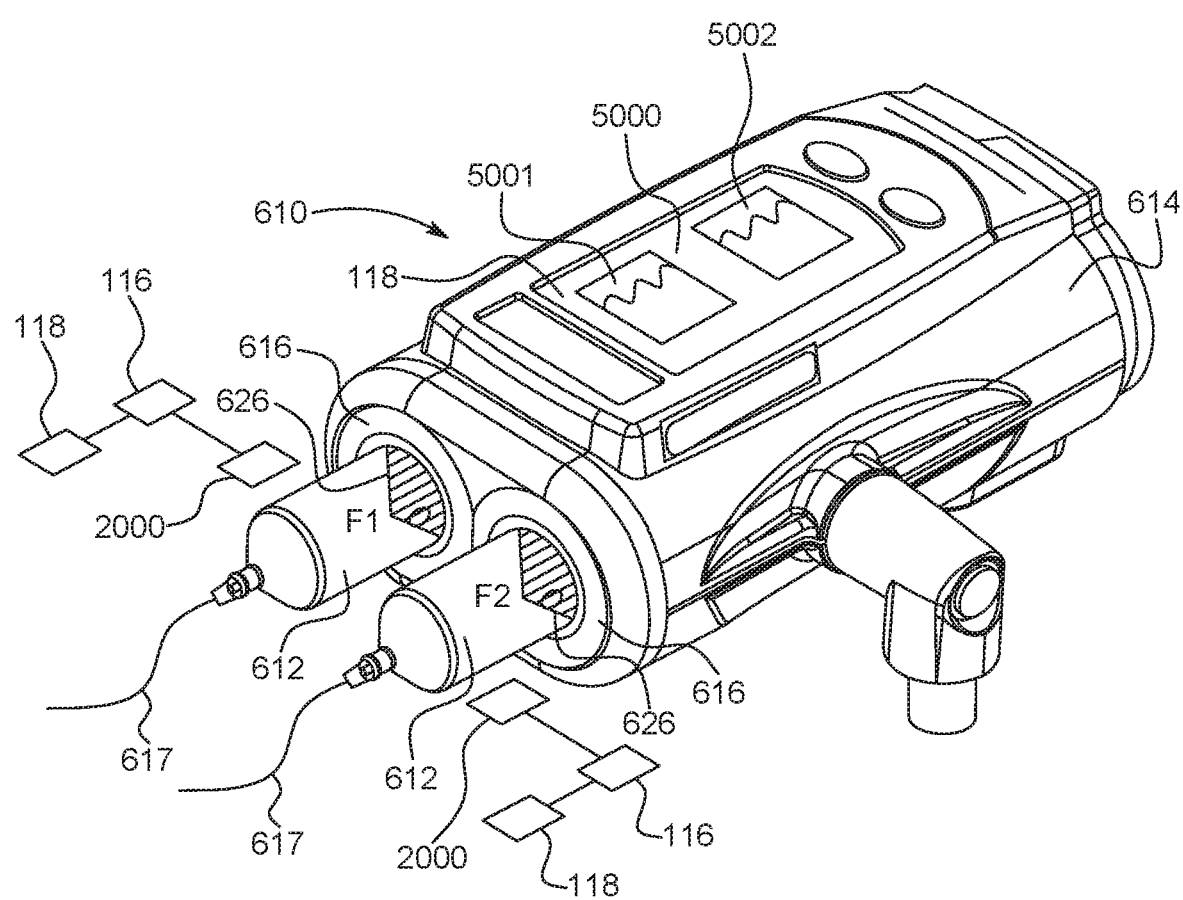
FIG. 1 is a top perspective view of an embodiment of a system including a fluid injector and at least one syringe.

For purposes of the description hereinafter, spatial orientation terms, as used, shall relate to the referenced example as it is oriented in the accompanying drawing figures or otherwise described in the following detailed description. Unless stated otherwise, reference numbers cited in a particular figure refer only to the features shown in that Figure. However, it is to be understood that the embodiments described hereinafter may assume many alternative variations and configurations. It is also to be understood that the specific components, devices, and features illustrated in the accompanying drawings and described herein are simply exemplary and should not be considered as limiting.

For purposes of the description herein, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe, the term "proximal" refers to the portion of a syringe nearest to an injector, when a syringe is connected to an injector. The term "distal" refers to the portion of a syringe farthest away from an injector. It is to be understood, however, that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the terms "electronic communication" and "electronically communicate" refer to the receipt or transfer of one or more signals, messages, commands, or other type of data. For one unit or device to be in communication with one or more other unit or device means that the one unit or device is able to receive data from and/or transmit data to the one or more other unit or device. An electronic communication may use a direct or indirect connection, and may be wired and/or wireless in nature. Additionally, two or more units or devices may be in electronic communication with each other even though the data transmitted may be modified, processed, routed, etc., between the first and second unit or device. For example, a first unit may be in electronic communication with a second unit even though the first unit passively receives data and does not actively transmit data to the second unit. As another example, a first unit may be in electronic communication with a second unit if an intermediary unit processes data from one unit and transmits processed data to the second unit. In non-limiting examples, an electronic communication may occur through one or more wired or wireless connections, such as, through one or more wires, through direct wireless protocols such as Bluetooth, Near Field Communication (NFC), or other radio frequency protocols, and/or through indirect wireless communication such as through a local Wi-Fi network or a secure Internet connection. Wireless communication may include, but is not limited to, any electronic communication that does not require direct wired contact between the two electronically communicating units or devices such as via a Wi-Fi network, communication via Bluetooth, NFC, other conventional wireless systems, or other non-wired electromagnetic communication systems. It will be appreciated that numerous other arrangements are possible.

It is to be understood that the term "fluid chamber" as it used in the present disclosure, is inclusive of the terms "syringe," "fluid container," and "drip chamber."

With reference to FIG. 1, an example of a fluid injector 610 (also referred to as "injector 610"), such as an automated or powered fluid injector, is adapted to interface with and actuate at least one syringe 612, each of which may be independently filled with a medical fluid F1 and F2, such as contrast media, saline solution, or any desired medical fluid. The injector 610 may be used during a medical procedure to inject the medical fluid F1,F2 into the body of a patient by driving a plunger 626 of the at least one syringe 612 with at least one piston. The injector 610 may be a multi-syringe injector, as illustrated, wherein several syringes 612 may be oriented in a side-by-side or other arrangement and include plungers 626 separately actuated by respective pistons associated with the injector 610. In certain aspects with two syringes 612 arranged in a side-by-side relationship and filled with two different medical fluids, the injector 610 may deliver fluid from one or both of the syringes 612 either independently (single flow) or simultaneously (dual flow).

With continued reference to FIG. 1, the injector 610 may have a housing 614 formed from a suitable structural material, such as plastic or metal. The housing 614 may have various shapes and sizes depending on a desired application. For example, the injector 610 may be a free-standing structure configured to be placed on the floor with a stationary or movable platform. Alternatively, the injector 610 may be configured for placement on a suitable table or support frame, or hung from the ceiling. The injector 610 includes at least one syringe port 616 for receiving the at least one syringe 612 to engage respective piston elements. In some aspects, the at least one syringe 612 includes at least one syringe retaining member for retaining the syringe 612 within the syringe port 616 of the injector 610. The at least one syringe retaining member (not shown) operatively engages a locking mechanism provided on or in the syringe port 616 of the injector 610 to facilitate loading and/or removal of the syringe 612 to and from the injector 610, as described herein. The syringe retaining member and the locking mechanism together define a connection interface for connecting the syringe 612 to the injector 610.

With continued reference to FIG. 1, at least one fluid path 617 may be fluidly connected with the at least one syringe 612 for delivering medical fluid F from the at least one syringe 612 to a catheter, needle, or other fluid delivery device (not shown) inserted into a patient at a vascular access site. Fluid flow from the at least one syringe 612 may be regulated by a fluid control module (not shown) comprising a processor. The fluid control module may operate various pistons, valves, and/or flow regulating structures to regulate the delivery of the medical fluid, such as saline solution and contrast, to the patient based on user-selected injection parameters, such as injection flow rate, duration, total injection volume, and/or ratio of contrast media and saline.

As schematically shown in FIG. 1, syringes 612 may be monitored by one or more sensors 2000 ("sensors 2000"). In an embodiment, sensors 2000 may comprise optical devices that are capable of measuring the change in fill volume in syringes 612 based on measuring one or more parameters associated with the syringes 612. In an embodiment, sensors 2000 may comprise one or more cameras. A sensor 2000 may observe the air liquid interface based upon reflection (including scatter) or transmission (including refraction) of light at that interface. The light may be supplied by a part of the injector, not shown, or may be ambient light. The sensor 2000 may observe the light that is transmitted through a syringe 612 from a pattern on the other side—for example a pattern according to the Medrad Fluidot indicator system, available from Bayer Medical Care Inc. of Indianola, Pennsylvania—or other scale or gradation patterns and thus estimate the fluid's optical index of refraction in addition to the presence and/or position of any fluid air interface, see also International Application Publication WO 2017/040154, incorporated herein by this reference. It is also to be understood that references to sensors 2000 according to the present disclosure may include a single sensor, or an array of multiple sensors. Sensors 2000 electronically communicate by a wired mechanism, or wirelessly, with a control module, or another processor 116 comprising appropriate image recognition software that can be used to automatically identify the remaining fill volume of the syringes 612 as an injection procedure is underway, without the need of a user to enter volume data into the control unit. In other embodiments, fewer or more sensors 2000 may be included in the fluid injector 610, as appropriate. In further non-limiting examples, syringes 612 may be equipped with a magnetic tag, magnetic tape, a bar code, RF-ID tag, a label such as a barcode or QR code, or other indicator which provides information about the mass, volume, or contents of the container, whether the contents of the container have passed their useful shelf life expiration date, or other information that is useful to the user. In an embodiment, a sensor for such a label may be situated in the at least one syringe port 616. In an embodiment, such information may be displayed on a graphical user interface ("GUI") 5000 (see also FIGS. 2 and 10) on a display 118. In an embodiment, real-time data of the change in volume, in syringes 612, calculated by a processor 116 may be displayed on the GUI 5000, as may be a warning when fill volumes approach a predetermined level, or the fluids have been exhausted. Calculated fill volumes may be shown numerically and/or graphically. Graphical representations 5001 and 5002 of fill volumes in syringes 12 are depicted on GUI 5000 in FIG. 1.

In an alternative embodiment, the fill volume of syringes 612 may be measured by their masses or by a correlation between the concentrations (g/mL) of a contrast agent dissolved in a volume of solvent to make up the contrast media solution. Syringes 612 may be in communication with measuring devices, not shown, that electronically communicate with a control module, or another processor comprising appropriate software to calculate the fill volume in the containers based on their masses during an injection procedure. In an embodiment, measuring devices may be included in the at least one syringe port 616.

Figure 2:
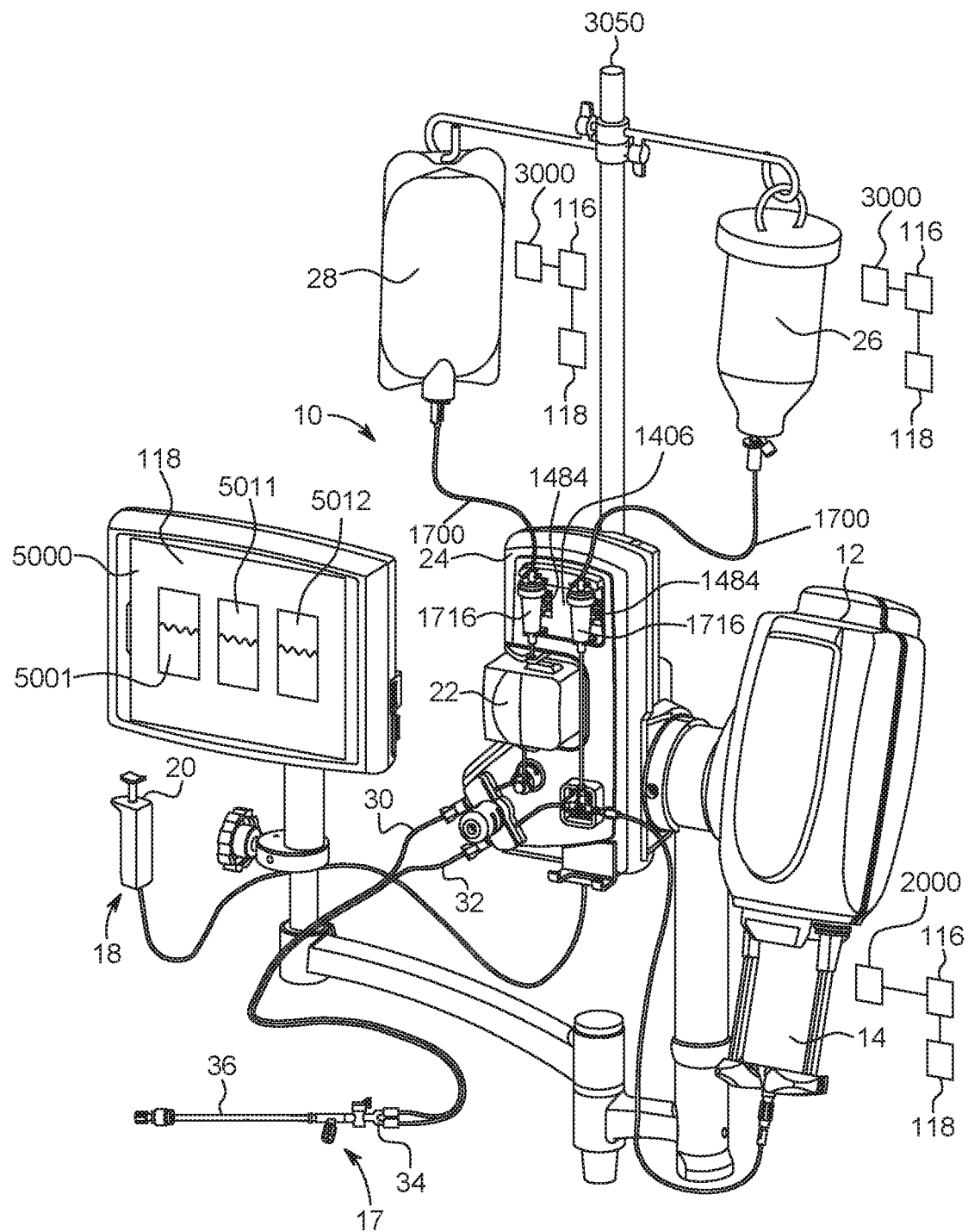
FIG. 2 is a perspective view of a fluid injection system in accordance with the present disclosure.

FIG. 2 is a perspective view of another fluid injector 10. The fluid injector 10 is used to deliver fluids to a patient during a medical injection procedure. For example, the fluid injector 10 may be used during an angiographic procedure to inject contrast media and common flushing agents, such as saline, into the body of a patient. An example of such a fluid injection or delivery system is disclosed in U.S. Pat. No. 7,094,216, the disclosure of which is incorporated herein by reference in its entirety.

As depicted in FIG. 2, fluid injector 10 generally may include a powered fluid injector 12 that is adapted to support and actuate a syringe 14 storing a first injection fluid for injection into a patient during a medical procedure, such as an angiographic procedure. The injector 12 is generally used to supply the contrast media under pressure to the fluid path set 17 and, ultimately, the patient. The injector 12 is optionally controlled by a hand controller 18 to supply the contrast media at discrete and preselected flow rates based on a physical input such as a trigger plunger 20. The fluid injector 10 further includes a second injection fluid that may be mixed with the first injection fluid prior to being delivered to a patient or delivered directly to the patient without mixing, depending on the mode of operation of the injector 12. The second fluid is advanced by a pumping mechanism 22 such as a peristaltic pump.

With further reference to FIG. 2, the powered injector 12 is operatively associated with a fluid control module 24. The fluid control module 24 is generally adapted to support the fluid path set 17. The fluid path set 17 is comprises one or more fluid path elements adapted to fluidly connect the syringe 14 to a container of contrast media 26 and a container of saline 28, which is supplied to the patient via the same catheter as the contrast media 26.

With further reference to FIG. 2, containers 26 and 28 of first and second injection fluids may be monitored by one or more sensors 3000 ("sensors 3000"). In an embodiment, sensors 3000 may comprise one or more optical devices that are capable of measuring the change in fill volume in containers 26 and 28, respectively. In an example, sensors 3000 may include one or more cameras. It is to be understood that references to "sensors" according to the present disclosure may include a single sensor, more than one sensor, a plurality of sensors, or an array of multiple sensors. Sensors 3000 electronically communicate, for example by a wired mechanism, a wireless mechanism, or a combination of wired and wireless mechanisms, with the control module 24, or another processor 116, comprising appropriate image recognition software that can be used to identify the remaining fill volume or amount of the containers as an injection procedure is underway, without the need of a user to enter volume or amount data into the control unit. While shown schematically in FIG. 2 as being external to the fluid control module 24, it is to be understood that examples of the processor 116 may physically reside in or proximate to the fluid control module 24.

In examples, fewer or additional sensors may be included in the fluid injector 10, as appropriate. Although schematically represented in FIG. 2, sensors 3000 may be positioned in the system 10 where they may measure the fluid level in containers 26 and 28. In an example, sensors 3000 may be positioned in or on a support pole 3050. Sensors 3000 may be configured to detect the change in level of a meniscus of a fluid in one or more of containers 26 and 28. In an embodiment, containers 26 and 28 may include measurement markers, and sensors 3000 may be configured to detect the position of a meniscus, or a liquid-gas interface, of the fluid in containers 26 and 28 relative to the measurement markers, which provides position data on the meniscus.

In further non-limiting examples, containers 26 and 28 may be equipped with a magnetic tag, magnetic tape, a bar code, RF-ID tag, a label such as a barcode or QR code, or other indicator which provides information about the mass, volume, and/or contents of the container, lot number and/or date of manufacture and/or whether the contents of the container have passed their useful shelf life expiration date, or other information that is useful to the user. In an embodiment, such information may be read and displayed on a GUI 5000 (see also FIG. 10) located on a display 118. In an embodiment, real-time data of the change in volume or amount in containers 26 and/or 28, calculated by a processor 116 in the control module 24 or another processor 116, may be displayed on the GUI 5000. In specific embodiments, a warning or alarm may be triggered when fill volumes approach a predetermined level, or the fluids have been exhausted. Graphical representations 5011 and 5012 of fill volumes in containers 26 and 28 are depicted on GUI 5000 in FIG. 2. Non-limiting examples of graphical representations 5011 and 5012 may include real-time video images of the fill volume levels in containers 26 and/or 28, or electronically-generated representations of fill volume levels.

In a non-limiting example, the fill volume of containers 26 and 28 may be measured by their masses. Containers 26 and 28 may be in communication with measuring devices, not shown, that electronically communicate with a processor in the control module 24, or another processor comprising appropriate software to calculate the fill volume in the containers based on their masses, for example using a weight percent (w/w %), weight per volume percent (w/v %), or a concentration (g/mL) of solute in solvent, during an injection procedure. A computation of the mass delivered for a given volume delivered may give an indication of density of the fluid and thus information on type of contrast or whether the fluid is saline.

With further reference to FIG. 2, a fill volume of the syringe 14 may be monitored by a sensor 2000. In an example, the sensor 2000 may comprise an optical device or optical devices that are capable of measuring the change in fill volume in the syringe 14. In an example, the sensor 2000 may include one or more cameras. The sensor 2000 electronically communicates by a wired mechanism, a wireless mechanism, or a combination of wired and wireless mechanisms, with the control module 24, or another processor 116 comprising appropriate image recognition software that can be used to identify the remaining fill volume of the syringe 14 as an injection procedure is underway, without the need of a user to enter volume or amount data into the control unit. In examples, the sensor 2000 may be stationary, or may be actuated to follow the changing fill volume level in the syringe 14, or may be comprised of one or more optical devices, such as cameras. The sensor 2000 may include a single optical device, or multiple optical devices configured to detect the change in fill volume of the syringe 14. An embodiment of the sensor 2000 may include an array of optical devices configured to detect the fill volume of the syringe 14. One or more optical devices of the sensor 2000 may be included with optics, such as lenses, that give the sensor 2000 a wide field of detection, or a narrow field of detection. In an example, the sensor 2000 may be configured to detect the change in level of a plunger position or a meniscus of a fluid in the syringe 14. In an embodiment, the syringe 14 may include measurement markers, and the sensor 2000 may be configured to detect the position of a plunger position or a meniscus of the fluid in the syringe 14 relative to the measurement markers, which provides position data on the plunger position or the meniscus. As with sensor 3000, sensor 2000 may electronically communicate by a wired mechanism, a wireless mechanism, or a combination of wired and wireless mechanisms, with the control module 24, or another processor 116 comprising appropriate image recognition software that can be used to identify the remaining fill volume of the syringe 14.

In further non-limiting examples, the syringe 14 may be equipped with a magnetic tag, magnetic tape, a bar code, RF-ID tag, a label such as a barcode or QR code, or other indicator which provides information about the mass, volume, and/or contents of the container, lot number and/or date of manufacture and/or whether the contents of the container have passed their useful shelf life expiration date, or other information that is useful to the user. In an example, such information may be displayed on a GUI 5000 (see also FIG. 10). In an embodiment, real-time data of the change in volume or amount in the syringe 14 may be calculated by a processor in the control module 24, or another processor, and may be displayed on the GUI 5000. In certain embodiments, a warning or alarm may be triggered when fill volumes approach a predetermined level, or the fluids have been exhausted. Graphical representations 5001 of the fill volume in the syringe 14 are depicted on the GUI 5000 in FIG. 2. Non-limiting examples of graphical representations 5001 may include a real-time video image of the fluid level in the syringe 14, or electronically-generated representations of fill volume levels.

The fluid path set 17 may be a single-use or multi-use disposable connection including a first input line 30 and a second input line 32, a downstream Y-connector 34 joining the first and second input lines 30, 32, and a catheter connector conduit 36. Aspects of the fluid path set 17 may be found in U.S. Pat. Nos. 7,094,216, and/or 7,556,619e.

Figure 3:
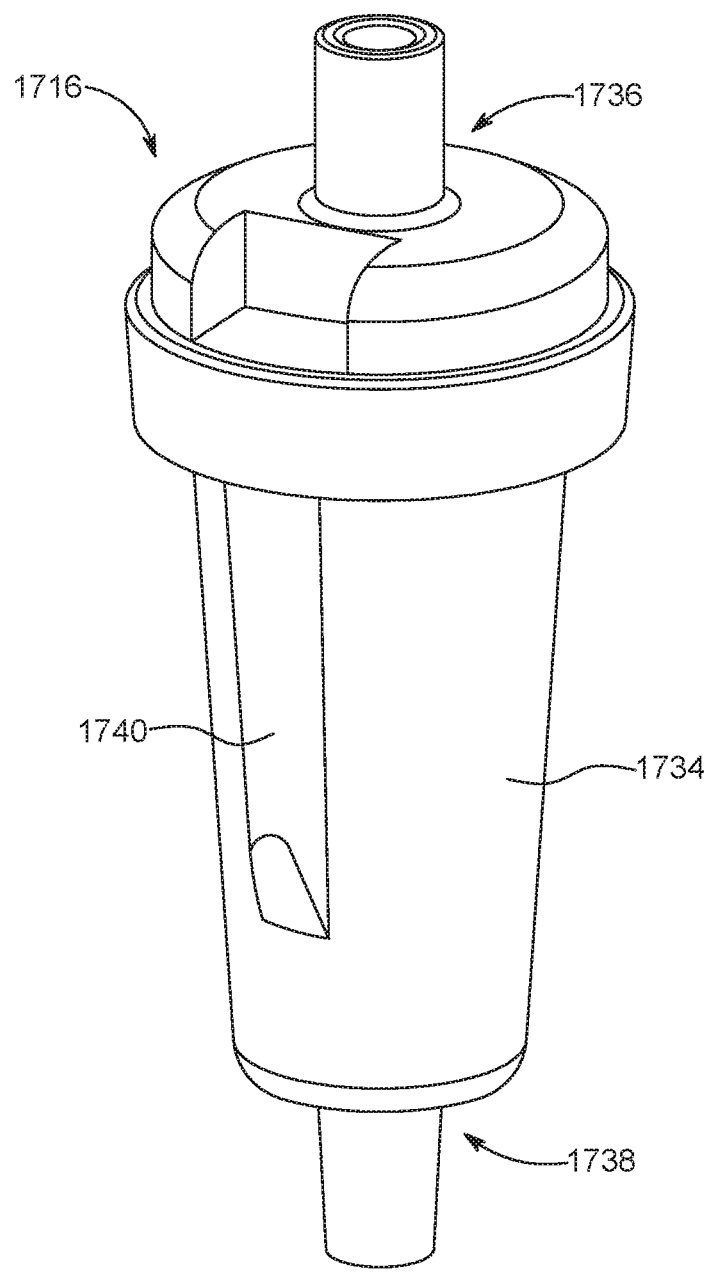
FIG. 3 is a perspective view of a drip chamber in accordance with an aspect of the present disclosure and adapted for use in the fluid injection system of FIG. 2.

Referring briefly to FIG. 3, an embodiment of a drip chamber 1716 used in the fluid injector 10 of FIG. 2 is shown in enlarged detail. The drip chamber 1716, shown in FIGS. 2 and 3, generally has an elongated body 1734 with a top end 1736 and a bottom end 1738. The body 1734 is formed with a projection 1740, which generally extends longitudinally, laterally along the body 1734, or in any configuration on the body 1734 of the drip chamber 1716, and may even be in the form of a handle with an opening such as those found on plastic bottles. The projection 1740 is generally provided to interact with one or more fluid level sensing mechanisms 1406, and may be referred to as a "back" window because the projection 1740 will generally face the fluid level sensors in the fluid level sensing mechanism 1406 when the drip chamber 1716 is associated with one or more fluid level sensing mechanisms 1406.

Figure 4:
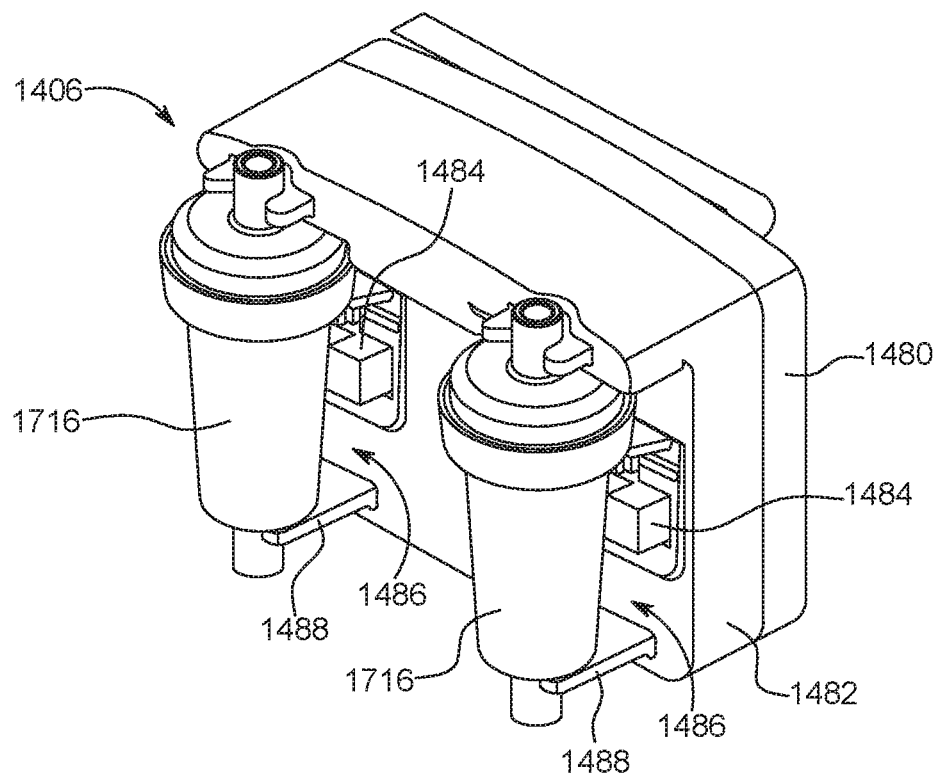
FIG. 4 is a perspective view of a fluid level sensing mechanism.
Figure 5:
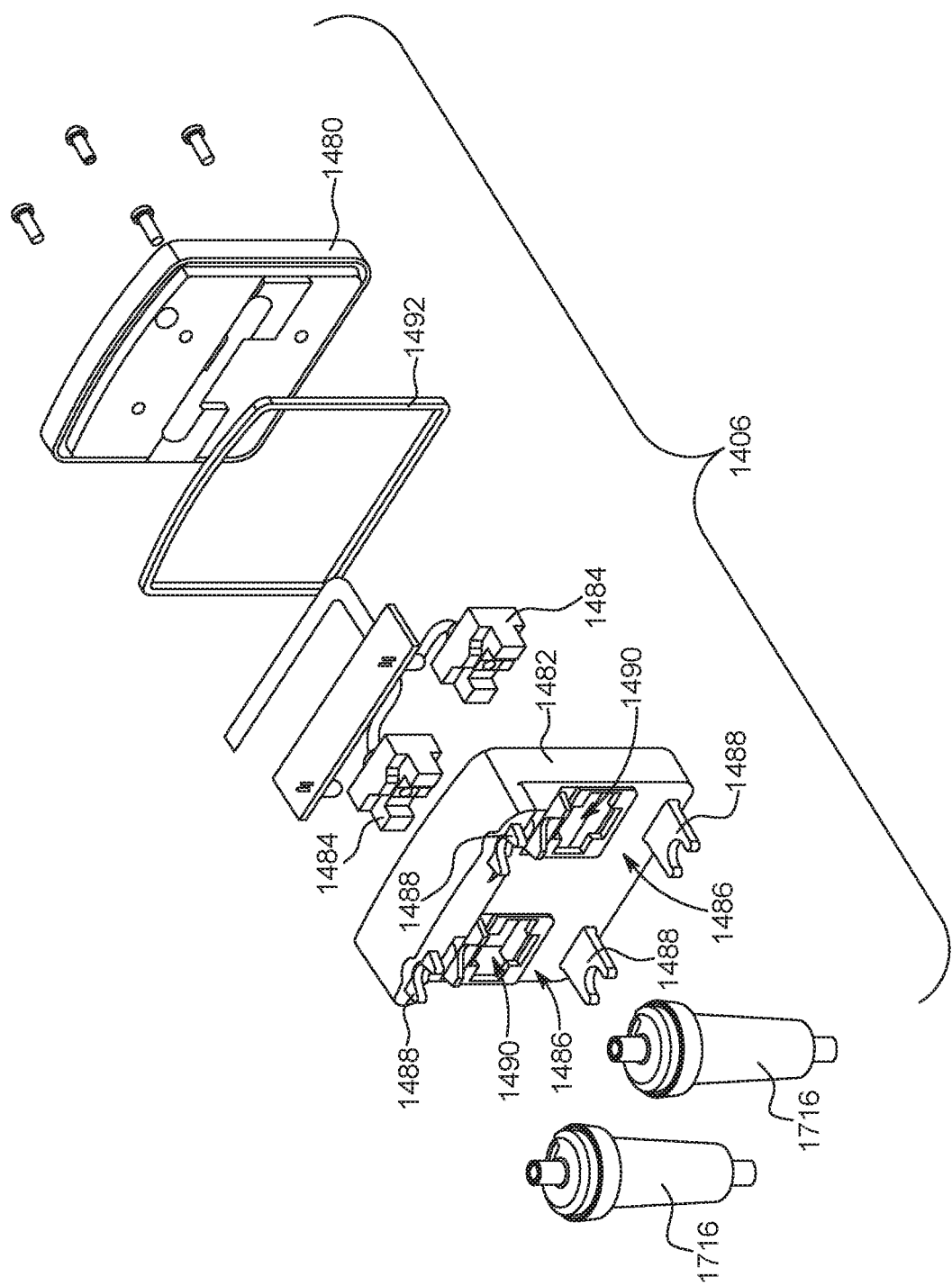
FIG. 5 is an exploded perspective view of a fluid level sensing mechanism of FIG. 4.

With reference to FIGS. 3 and 4, the body 1734 is preferably formed of a plastic material and, more particularly, a resiliently deformable medical-grade plastic material to allow in-place "priming" of the drip chamber 1716 by squeezing, when the drip chamber 1716 is associated with a fluid level sensing mechanism 1406. The at least one fluid level sensing mechanism 1406 may be adapted to support and secure the drip chambers 1716, or may be offset from the drip chambers 1716. In an embodiment, the projection 1740 further permits the drip chamber 1716 to be primed in place in the fluid level sensing mechanism 1406. The plastic material comprising the body 1734 may be substantially clear or slightly opaque, but the projection 1740 is preferably clear to allow an optical fluid sensor in the fluid level sensing mechanism 1406 to detect the fluid level in the drip chamber 1716. In another embodiment, the material comprising the body 1734 may be comprised of a transparent or translucent material, to allow an optical fluid sensor in the fluid level sensing mechanism 1406 to detect the fluid level in the drip chamber 1716. The projection 1740 is preferably raised from the body 1734 of the drip chamber 1716 to allow priming of the drip chamber 1716. Generally, the body 1734 of the drip chamber 1716 is sufficiently clear to allow light transmission from lighting associated with the fluid level sensing mechanism 1406. The body 1734 of the drip chamber 1716 will generally act as a light conduit or "light pipe" that will illuminate the fluid flow path in the medical tubing forming the output lines 1718 associated with the drip chambers 1716 connected to containers 26 and 28.

Referring to FIGS. 4-7, an embodiment of a fluid level sensing mechanism 1406 configured to be provided on a fluid control module is shown in greater detail. The fluid sensing mechanism 1406 generally interfaces with the drip chambers 1716 associated with the containers 26 and 28. The fluid sensing mechanism 1406 is provided to indicate to the operator of the fluid injector that sufficient injection fluid, either primary contrast media or secondary saline, is available for an injection or flushing procedure. The fluid sensing mechanism 1406 is generally adapted to warn the operator when the fluid level in the drip chambers 1716 is below a level sufficient to conduct an injection procedure. During filling or priming, the operator may squeeze the drip chamber 1716 so that some of the air in the drip chambers 1716 moves up into the containers 26 and 28 and the fluid level, the liquid-gas interface, is at or above the desired level as measured by the fluid sensing mechanism 1406. The fluid sensing mechanism 1406 is provided as a safety feature to ensure that air is not introduced into the fluid path set 1700 during an injection procedure or flushing procedure involving the fluid injector.

The fluid sensing mechanism 1406 generally includes a support plate 1480, a drip chamber support 1482, and one or more fluid level sensors 1484 (hereinafter "fluid sensors 1484") which are adapted for association with the drip chambers 1716 connected to the fluid containers 26 and 28. The support plate 1480 generally supports the various components of the fluid sensing mechanism 1406. The drip chamber support 1482 is generally secured to the support plate 1480 by suitable mechanical fasteners or another suitable attachment or mounting scheme. The drip chamber support 1482 may be a unitary structure that is integrally molded of plastic material, and includes a plurality of attachment or support locations 1486 adapted to support the drip chambers 1716. In particular, the drip chamber support 1482 may include snap mounts or positions 1488 for securing the bodies 1734 of the drip chambers 1716 in the fluid sensing mechanism 1406, and operatively associated with the fluid sensors 1484. The snap mounts 1488 may be adapted to engage inlet and outlet ports of the drip chambers 1716, as shown in FIG. 6.

In a non-limiting example, the drip chamber support 1482 defines respective openings 1490 for receiving the fluid sensors 1484, and associating the fluid sensors 1484 with the drip chambers 1716. The openings 1490 are positioned to allow the fluid sensors 1484 to be operatively associated with the projection 1740 formed on the bodies 1734 of the respective drip chambers 1716. As shown in FIG. 6, the fluid sensors 1484 may physically contact the projections 1740 on the drip chambers 1716, when the drip chambers 1716 are secured in the support locations 1486 on the drip chamber support 1482. Non-limiting examples of the fluid sensors 1484 include optical or ultrasonic sensors. It also is to be understood that references to fluid sensors 1484 according to the present disclosure may include a single sensor, or an array of multiple sensors. A suitable ultrasonic sensor for the fluid sensors 1484 is manufactured by Omron. A gasket 1492 may be provided between the drip chamber support 1482 and the support plate 1480 to prevent fluid intrusion between the drip chamber support 1482 and the support plate 1480, which could damage the fluid sensors 1484. Lights 1494 may be associated with the support locations 1486 to illuminate the drip chambers 1716. The lights 1494 are further adapted to visually indicate when the fluid level in the drip chambers 1716 drops below a predetermined level during operation of the fluid injector, for example by changing modes to an intermittent mode and blinking to indicate to the operator that insufficient fluid is available for an injection procedure. The lights 1494 provide "back-lighting" for not only the drip chambers 1716 but also the medical tubing associated with the drip chambers 1716, and light the medical tubing and drip chambers 1716 in such a manner that the medical tubing and the drip chambers 1716 form a "light pipe" that illuminates at least part if not all of the first section 1710 of the fluid path set 1700. The back lighting allows the operator of the fluid injector to easily visually inspect the drip chambers 1716 to check the fluid level present in the drip chambers 1716.

The fluid sensors 1484 are generally adapted to provide fluid position signals to the computer hardware/software associated with the fluid control module and/or injector to indicate the fluid levels in the drip chambers 1716. Position of the liquid-gas interface in the drip chamber changes as a function of the amount of fluid in the associated fluid container 26 or 28. The fluid sensors 1484 may be further adapted to initiate an alarm signal to the computer hardware/software associated with the fluid control module and/or the injector when the fluid level in the drip chambers 1716 falls below a predetermined level. The computer hardware/software associated with the fluid control module and/or the injector may be adapted to respond to the alarm signal by halting the on-going injection procedure.

Figure 6:
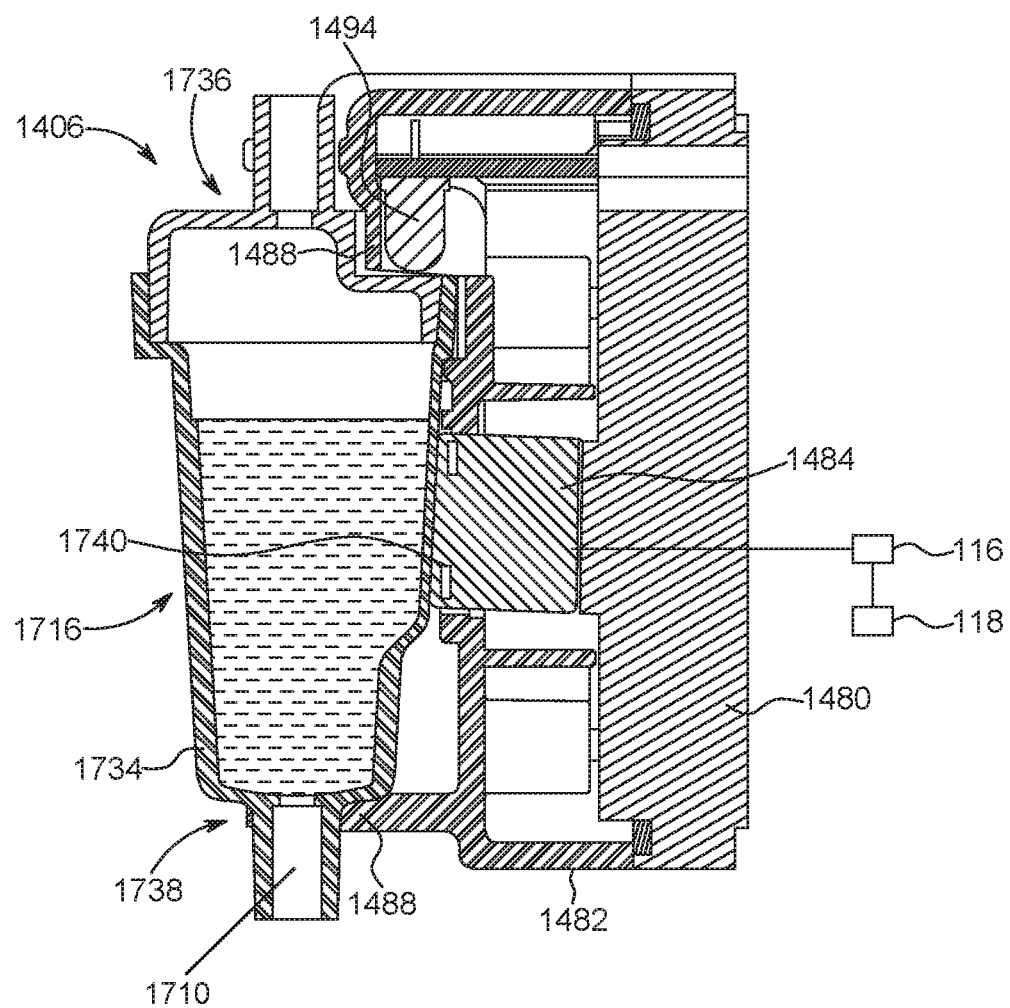
FIG. 6 is a transverse cross sectional view of a fluid level sensing mechanism of FIG. 4.

As illustrated in an embodiment depicted in FIG. 6, the fluid sensors 1484 are tilted or angled at a slight or small angle relative to a vertical axis generally parallel to the face of the support plate 1480. The slight angle, for example, is selected to complement the projection 1740 on the bodies 1734 of the drip chambers 1716. The projection 1740 on the bodies of the drip chambers 1716 is preferably tapered at a small angle, such as 3 degrees. The projection 1740 on the bodies 1734 of the drip chambers 1716 is preferably tapered inward at a small angle from the top end 1736 to the bottom end 1738 on the drip chambers 1716, as illustrated in FIG. 6. The fluid sensors 1484 are positioned in the openings 1490 to complement the tapered projections 1740 on the respective drip chambers 1716, and preferably physically contact the projections 1740 as indicated previously.

Figure 7:
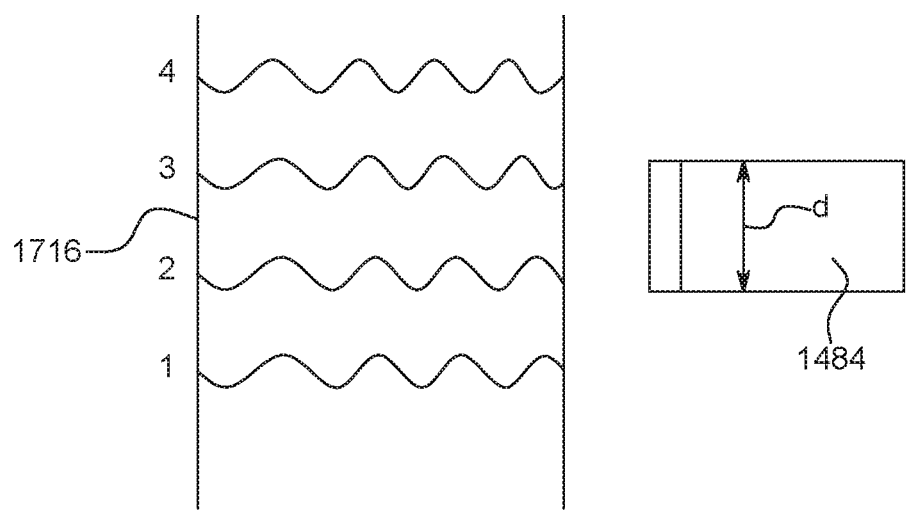
FIG. 7 is a schematic view of a fluid chamber and sensor according to the present disclosure.

FIG. 7 shows a schematic view of a cross section of drip chamber 1716. While this Figure contemplates a drip chamber, it is to be understood that the description herein may apply to determining fluid levels in other fluid chambers, such as containers 26 and 28, with sensors 3000 as well. Multiple possible fluid levels 1, 2, 3, 4 are shown in the drip chamber 1716. An exemplary single sensor 1484 of an embodiment of a fluid sensing mechanism 1406 is depicted. The sensor 1484 has a height d. As can be seen from the Figure, the position and height of the single sensor 1484 makes it well disposed to detect and measure the changes in the liquid-gas interface in the drip chamber 1716 when the fluid is at or above level 2. However, as fluid drops below level 2, the exemplary single sensor 1484 may not detect or measure the liquid-gas interface well. Similarly, when the fluid is at or above level 4, changes in fluid level may not be detected by the fluid sensing mechanism 1406.

Monitoring the location of a liquid-gas interface, such as the location of a meniscus, is superior to monitoring the presence or absence of fluid because it allows additional functionalities. For example, in an embodiment, by tracking the direction and/or the rate of travel of the liquid-gas interface, that information can be compared to the fill rate of the drip chamber to assess whether the fluid source has been depleted, disposable integrity, the fill pressure drop, the type of fluid being filled, and venting in the container, 26 or 28.

Figure 10:
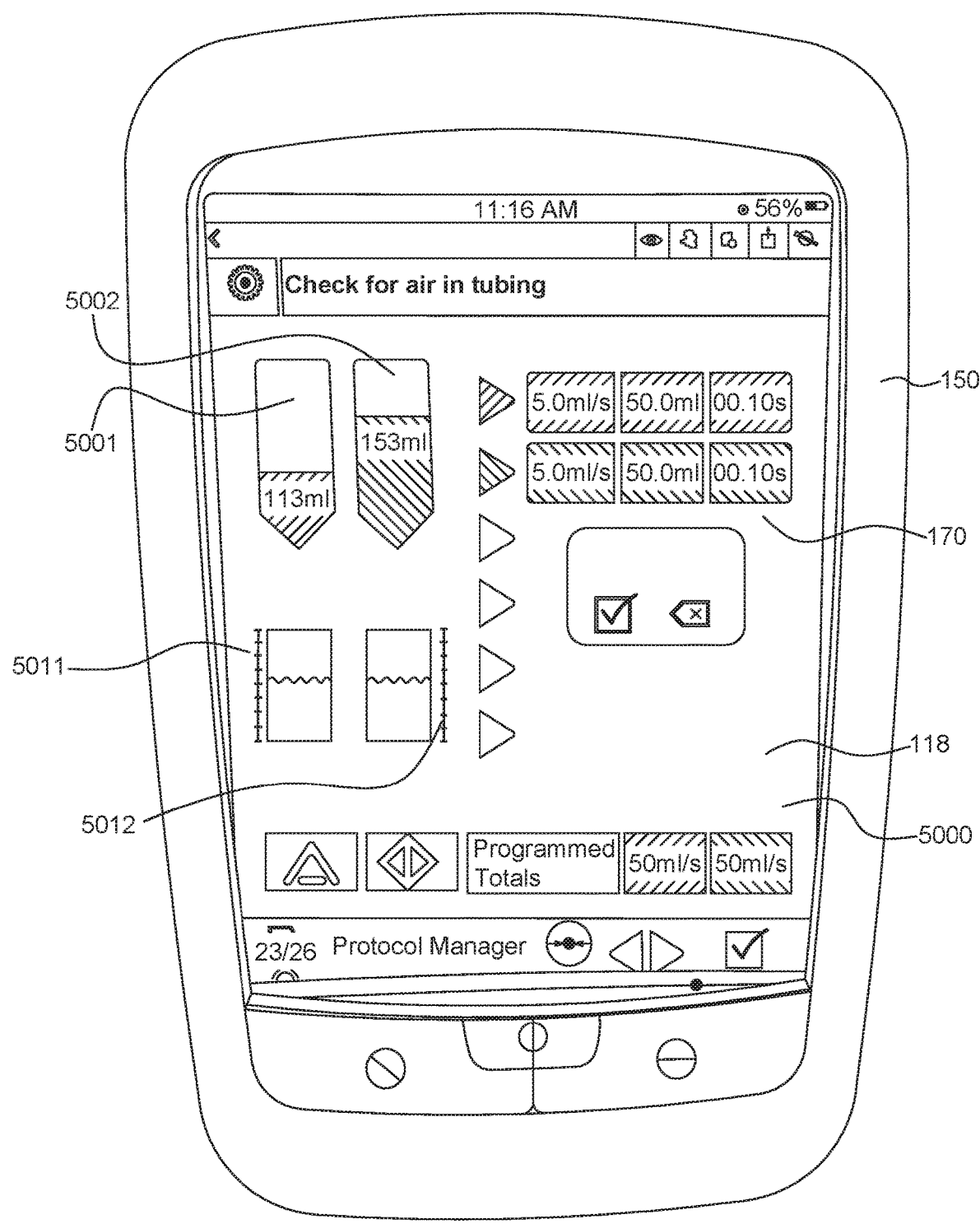
FIG. 10 is a schematic view of a user interface for a fluid injection system according to the present disclosure.

By way of a non-exhaustive list of examples, if the liquid-gas interface falling rate and/or steady state or equilibrium filling position matches that expected for the injection filling rate within a pre-determined error band, this may indicate normal filling operation. If the liquid-gas interface is falling at a rate, or to a position, that is known to coincide with that of an empty supply, that may be an indication that the fluid source has been depleted. If the liquid-gas interface is falling at a rate or to a position not commensurate with the filling rate, it may indicate an obstruction with the supply venting or a clogged spike filter. If, after the filling stops, the liquid-gas interface is not rising at a rate or a level commensurate with the normal drip chamber filling rate, it may indicate that the fluid container, 26 or 28 is not properly vented. The movement and/or level of the liquid-gas interface or fluid amount may also be used as input to the injector control system or other means to adjust or affect the fill rate in a closed loop or open loop fashion. Any or all of these conditions may be displayed for an operator on a GUI 5000 on a display 118, as seen in FIG. 10, or result in an audible alarm, in order to notify the operator of the condition, or a processor 116 or the fluid control module 24 automatically enabling or preventing the injector 10 from performing an action.

In an embodiment, the liquid-gas interface level may be monitored for the purpose of permitting a "smart fill" process. The injector filling operation could tie the servo control to the liquid-gas interface position and speed up or slow down the filling as needed. This would allow the operator to fill lower viscosity contrast agents and saline at a faster rate, thus optimizing workflow. This feature could not only self-compensate for high viscosity fluids, but may also manage variation in bottle sizes, venting performance, heating, disposable set variation, and other benefits as well.

Figure 8A:
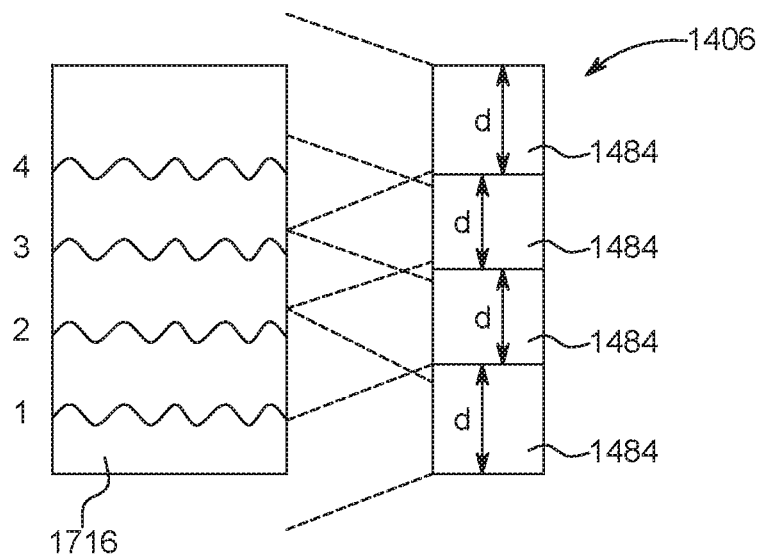
FIG. 8A is a schematic view of a fluid chamber and sensor arrangement according to the present disclosure.

FIG. 8A shows a schematic view of a cross section of a drip chamber and a non-limiting example of a fluid sensing mechanism 1406. According to the example, the fluid sensing mechanism 1406 includes an array of sensors 1484 configured to detect a liquid-gas interface at multiple levels in the drip chamber 1716. As shown, each sensor 1484 has a height d; however, sensors 1484 of differing heights could be used. Four sensors 1484 are shown to make the array; however various numbers of sensors could be used. For example, a linear array of sensors or a two dimensional array such as a camera may be used. In the case of optical sensors, sensors 1484 may be outfitted with optics to give them separated, contiguous, or overlapping fields of detection. The dashed lines of FIG. 8A represent the fields of detection of the sensors 1484. The sensors 1484 are in electronic communication with a processor, and software could be used to determine the level of the liquid-gas interface, and changes therein, with a higher degree of accuracy and over a greater range, than if just a single sensor 1484 were used. This could be accomplished, for example, by comparing the signal strengths and/or changes in the signal strengths of the various sensors 1484 in the array to each other, to a composite of the total signal, or to some otherwise determined level.

Figure 8B:
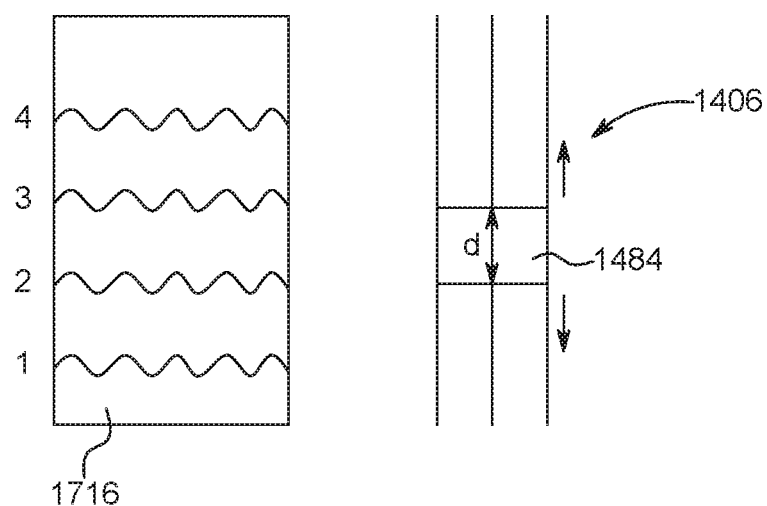
FIG. 8B is a schematic view of another fluid chamber and sensor arrangement according to the present disclosure.

In an embodiment depicted in FIG. 8B, a single sensor 1484 may be actuated or moved to follow the liquid-gas interface based on changes in the signal strength. Position data of the sensor 1484 may be communicated to a processor, and from those data, the level of the liquid-gas interface in drip chamber 1716 may be calculated by a processor. An array of sensors 1484 may also be actuated.

In embodiments depicted in both FIGS. 8A and 8B, the fluid sensing mechanism 1406 may be positioned closely to the drip chamber 1716, or be offset a distance from it, in order to give sensors 1484 a wider field of detection. The fluid sensing mechanism 1406 may be configured to support the drip chamber 1716, or may be situated by the drip chamber 1716 without supporting it.

It is to be understood that examples according to FIGS. 7 and 8A-8B may be applied to sensors 3000 configured to detect fill volumes in containers 26 and 28 as well.

With reference to FIGS. 2, 4-7, and 8A-8B, the fluid injector 10 may be configured as an image recognition system that includes at least one sensor 3000 and/or 1484, such as an image capture device, positioned having a field of detection directed to a container 26, 28; a processor 116 including a controller operatively connected to the sensor 3000 and/or 1484 and configured to process the images obtained from the sensor 3000 and/or 1484 using suitable image processing software; and a display 118 operatively connected to the processor 116 for displaying the results of the image processing performed by the central processing unit. In one example, the image processing software may be the Insight Explorer software from Cognex Corporation of Natick, Mass. and the sensor 3000 and/or 1484 may be a DataMan 100 camera also from Cognex Corporation. In addition, the at least one sensor 3000 and/or 1484 and the processor 116 may be integrated into a single component or provided as individual components. Further, the at least one sensor 3000 and/or 1484, the fluid injector 10, the display 118, and/or the processor 116 may be in wired communication or may communicate wirelessly, for example via Bluetooth, Wi-Fi, or other conventional wireless communication technology, or combination of various wired and/or wireless communication methods. Further, with reference to FIGS. 1 and 2, it is to be understood that the above examples of software and configuration may be used for sensors 2000 as well.

In another example, with reference to FIGS. 2, 4-7, and 8A-8B the sensors 3000 and/or 1484 can be an alternative type of sensor, such as an electromagnetic radiation detector, ultrasonic detector, or other suitable sensor as is known in the art, or even combinations of the various sensor types described herein. In some examples, the at least one sensor 3000 and/or 1484 is a digital camera that can be configured to obtain a digital image of a liquid-gas interface in a container 26, 28, and/or a drip chamber 1716, respectively. In other examples, the at least one sensor 3000 and/or 1484 can be an infrared radiation detector, ultraviolet light detector, ultrasound imaging device, or any other suitable sensor for identifying electromagnetic radiation emitted from an electromagnetic radiation source, not shown. With reference to FIGS. 1 and 2, it is to be understood that the above configuration may be used for sensors 2000 as well.

As will be appreciated by one of ordinary skill in the art, the at least one sensor 3000 and/or 1484 or detector can be adapted specifically for identifying a wavelength of electromagnetic radiation or light associated with an electromagnetic radiation source, not shown, and the illuminated identification pattern produced therewith. For example, the at least one sensor 3000 and/or 1484 can include various filters or tuned or attenuated optical elements for identifying only radiation within an expected wavelength (e.g., electromagnetic radiation within a wavelength emitted by the electromagnetic radiation source). Additionally, the containers 26, 28, the projection 1740 of the drip chamber 1716, or the drip chamber 1716 themselves can be used as filters by altering the material properties (e.g., color, molecular alignment, pigment additive, polarized surface) to filter light of a given wavelength to achieve an optimized visualization by the user. Alternatively, image processing techniques can be used to remove portions of obtained images outside of the expected wavelength, thereby reducing an influence of ambient light and increasing sensitivity for the illuminated identification pattern. With reference to FIGS. 1 and 2, it is to be understood that the above configuration may be used for sensors 2000 as well.

FIG. 10 shows a GUI 5000 of a display 118 on a user interface 150 in accordance with a non-limiting example of the present disclosure, showing various injection parameters 170 for an injection procedure, displayed on a touch screen. As described herein and/or known to those skilled in the art, the various parameters 170 may be monitored, changed, or inputted by the user before, during, or after an injection procedure, for example by touching the appropriate field on the touch screen and entering the appropriate data using an electronic keypad that appears on the touch screen. In certain examples, some or all of the parameters may be saved and uploaded to a patient records database either wirelessly or by wired connection from the user interface or another computer, for example a hospital information system or network. In non-limiting configurations, various parameters may be saved and uploaded automatically and/or in response to a user command. Graphical representations 5001 and 5002 of liquid-gas interfaces and/or plunger positions in syringes 612 or 14, and/or graphical representations 5011 and 5012 of liquid-gas interfaces in drip chambers 1716 or containers 26, 28 may be shown on the GUI 5000 in FIG. 10, and may be updated in real time, or at pre-determined time intervals, based on data provided by the sensors 1484, 2000, 3000. The GUI 5000 may show graphical representations of single or multiple syringes, and/or containers, and/or drip chambers 1716, depending on the needs of the user. In examples, a user may be able to choose which liquid-gas interface levels to display on the GUI 5000. Non-limiting examples of graphical representations 5001, 5002, 5011, and 5012 may include real-time video images of liquid-gas interfaces in drip chambers 1716 and/or containers 26, 28 as well as plunger position and/or or gas presence in syringes 14 or 612, or electronically-generated representations of liquid-gas interface levels, for example such that the user may check or confirm visually. As shown in FIG. 10, graphical representations of liquid-gas interface levels in drip chambers may be accompanied by numerical values as well. Alternatively, the GUI 5000 may show only numerical values of liquid-gas interface levels. Additional data, such as the rate of change liquid-gas interface levels, also may be displayed on the GUI 5000. Alternatively, the GUI 5000 may blink or give some other visual indication of any alarm or other states of the system, for example those discussed herein in relation to the activation of the light associated with the drip chambers 1716. Optionally the displayed color of the fluid, the fluid shape outline, or some other on screen indication may change color based upon the amount of fluid, for example green when full, yellow when in an intermediate range and red when in the lowest range.

Figure 9A:
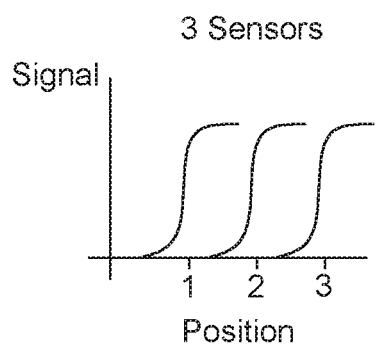
FIG. 9A is a graphical representation of signal strength as a function of a liquid-gas interface position according to an example according to the present disclosure comprising three sensors.
Figure 9B:
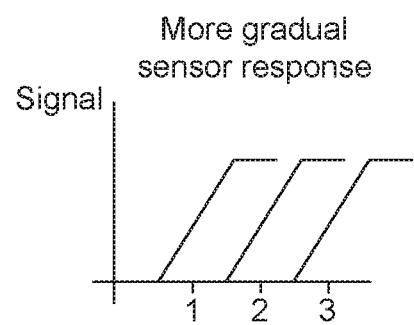
FIG. 9B is a graphical representation of signal strength as a function of a liquid-gas interface position according to an example according to the present disclosure comprising three sensors with a more gradual sensor response than in FIG. 9A.

With reference to FIGS. 1, 2, and 6, sensors 2000, 3000, and 1484 may comprise one or more electro-magnetic sensors, photosensitive detectors, ultrasonic sensors, or any sensor known in the art that may be used to detect the position of the liquid-gas interface and/or plunger position, or combinations of different sensor types. One non-limiting example of a detection mechanism including a sensor according to the present disclosure includes a beam of electromagnetic energy, such as visible, ultraviolet, or infrared light, passing through the fluid in a fluid chamber to a photosensitive sensor. In such a configuration, the beam is transmitted whether there is air or liquid in its path, but the intensity of the beam received by the sensor will be affected if the liquid-gas interface is in the beam's path. FIG. 9E depicts a graphical representation of signal strength as a function of the position of the liquid-gas interface using a configuration of three such sensors. However, it should be understood that some examples may include more or fewer sensors.

With continuing reference to FIG. 9E, the dips in signal strength on the graph correspond to situations wherein the liquid-gas interface passes within the field of detection of a sensor. In such a configuration, the apparatus according to the present disclosure may allow a user and/or the system to determine the position of the liquid-gas interface at various critical points in the filling process, depending on the positioning of the sensors according to this example.

In another example, the sensors may differentiate between the presence and absence of liquid in its field of detection. A non-limiting example of such a sensor is an ultrasonic sensor. FIGS. 9A-9D show graphical depictions of signal strength as a function of position of a liquid-gas interface in various configurations of sensors using sensors that differentiate between the presence and absence of liquid in their fields of detection. In such a configuration, as the liquid-gas interface passes through the field of detection, the signal changes from low to high or high to low.

Figure 9C:
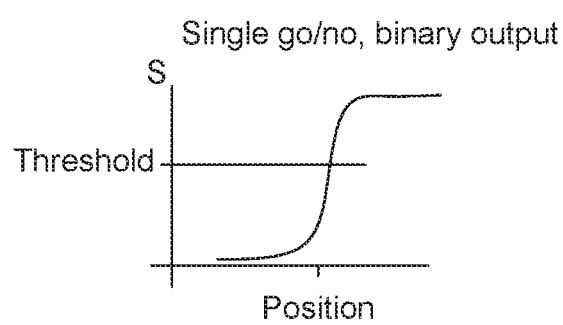
FIG. 9C is a graphical representation of signal strength as a function of a liquid-gas interface position according to an example according to the present disclosure comprising one sensor.

FIG. 9C depicts signal strength for a configuration using one such sensor with a narrow field of detection. As the liquid-gas interface passes through the field of detection of the sensor, the signal strength changes relatively rapidly for a change in interface position. Sensors according to this example allow a user to determine whether the liquid-gas interface is above or below the field of detection of the sensor. A sensor with a response as shown in FIG. 9C which responds fully over a relatively small range compared to the full range of fluid in the fluid chamber may be considered to be a point or a zero dimensional or "0D" sensor. In a non-limiting embodiment, the sensor may be actuated and, for example, oscillate between an upper and lower position, for example by adjustments in fluid flow rate, allowing the liquid-gas interface to pass repeatedly through the field of detection of the sensor. This may be referred to as "dithering" in the art. Dithering returns data on the position of the liquid-gas interface because the signal strength of the sensor will change as the sensor's field of detection crosses the liquid-gas interface. Dithering effectively makes a zero dimensional sensor a one dimensional sensor. The sensors 2000, 3000, and/or 1484 according to this example may be configured to dither between set positions that correspond to desired fluid levels within the container. If data indicate that the liquid-gas interface is lower or higher than a desired level for too long or moves with an inappropriate rate, an error value may be returned, and/or an alarm could be sounded alerting the user of the error and optionally providing a proposed solution to the error alert. A processor 116 may stop, change or enable an action according to such data. This is especially important in the case that the data returned by the sensor indicates that the liquid-gas interface is lower than the desired level, because it may indicate that an insufficient amount of liquid is in the fluid chamber.

Figure 9D:
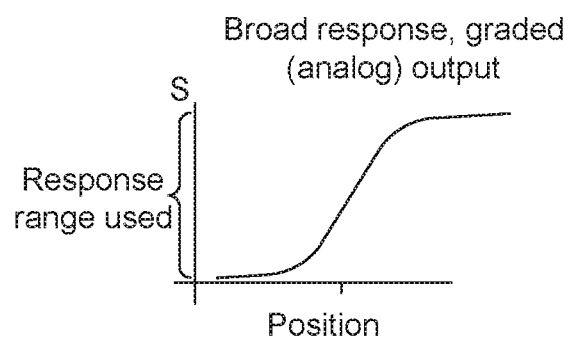
FIG. 9D is a graphical representation of signal strength as a function of a liquid-gas interface position according to an example according to the present disclosure comprising one sensor with a more gradual sensor response than in FIG. 9C.
Figure 9E:
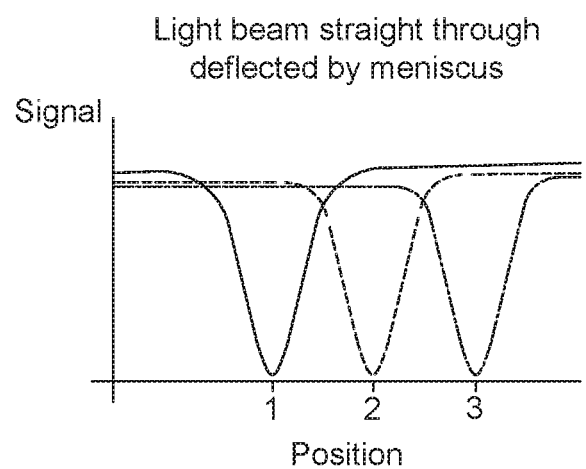
FIG. 9E is a graphical representation of signal strength as a function of a liquid-gas interface position according to another example according to the present disclosure.

FIG. 9D depicts a graphical representation of signal strength of a single sensor in a configuration using a sensor with a wider field of detection, or a more gradual response than that used in FIG. 9C. In an embodiment according to this configuration, as the liquid-gas interface travels through the field of detection of the sensor, there is a more gradual relationship between the position of the liquid-gas interface and the signal output of the sensor. In an example according to this configuration, data returned by the sensor may be generally proportional or univariately related to the position of the liquid-gas interface over a range of the sensor's field of detection, and the sensor's reading may be used to assess the position of the liquid-gas interface. In an example, the sensor's reading may also be used to determine a range of dithering, and/or to trigger error states, alarms, and/or the allowance or cessation of an action by the injection system. A single sensor with an extended field of detection may be sufficient to provide a one dimensional measurement that is used to determine the liquid gas interface position in the fluid chamber or container. A scale or other mass (or weight) determining sensor may also be configured to have a response as shown in FIG. 9D. A time of flight ultrasound or sound transducer measuring the sound transmission and reflection time from the bottom or top of the fluid container respectively to the fluid interface may be configured to have a response as shown in the figure as well. Other single sensor fluid level systems know in the art may be configured to have a response such as shown in FIG. 9D. Sensors such as listed here, a one dimensional optical array, a two dimensional optical array (for example, a camera) as well as sensors known to those skilled in the art may provide the 1D or one dimensional measurement that serves as input to determining the fluid fill of the fluid chamber.

Figure 9F:
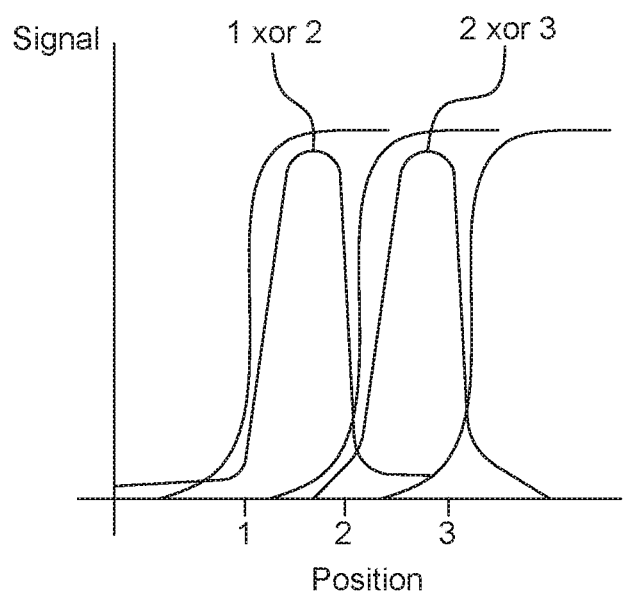
FIG. 9F is a graphical representation of signal strength as a function of a liquid-gas interface position according to another example according to the present disclosure.

It may be preferable to configure the fluid sensors 2000, 3000, 1484 to detect liquid-gas interface at a plurality of levels. FIG. 9A shows a graph depicting signal strength in a configuration of three sensors 1484 as a function of the position of the liquid-gas interface in a fluid chamber. It is to be understood, however, that such a configuration may be used with respect to sensors 2000, 3000. FIG. 9A shows a graphical depiction of signal strength for a configuration using three sensors that differentiate between the presence and absence of liquid, with narrow fields of detection. However, it should be understood that more or fewer sensors may be used. In the configuration according to FIG. 9A, information returned by the sensors indicates whether the liquid-gas interface is above or below the levels of a container within the fields of detection of the sensors. A position of the liquid-gas interface may be determined by comparing sensor signals. This comparison may be made by using an exclusive-or gate, which also may be referred to as an "xor" or "exor" gate in the art. As depicted in FIG. 9F, the output of the xor gate is high when one, and only one, of the two signal outputs that it compares is high. Thus, when the output of sensor one is high, but sensor two is not, then the signal retuned from the xor gate comparing sensors one and two would be high. If the signal detected by sensors one and two of this configuration both are low or high, then the xor gate comparing sensors one and two is low. Similar results are returned for the xor gate comparing sensors two and three. Thus, the use of one or more xor gates provides data on the position of the liquid-gas interface.

Thus, a configuration of two sensors with narrow fields of detection allows for the detection of whether the liquid-gas interface is below both, between the two (which may correspond to a controlled, or optimum, range of fluid levels in the container), or above both. In a further embodiment, a third, middle sensor may be provided between an upper and a lower sensor. This middle sensor may be actuated to allow it to move slightly, to provide more precise data on the position of the liquid-gas interface in the space between the fields of detection of the upper and lower sensors.

FIG. 9B depicts a graphical representation of signal strength of a sensor for a configuration using a sensor with a wider field of detection, or more gradual transition than that used in FIG. 9A. The fields of detection or regions of transition may be separated, contiguous, or overlapping.

Figure 11:
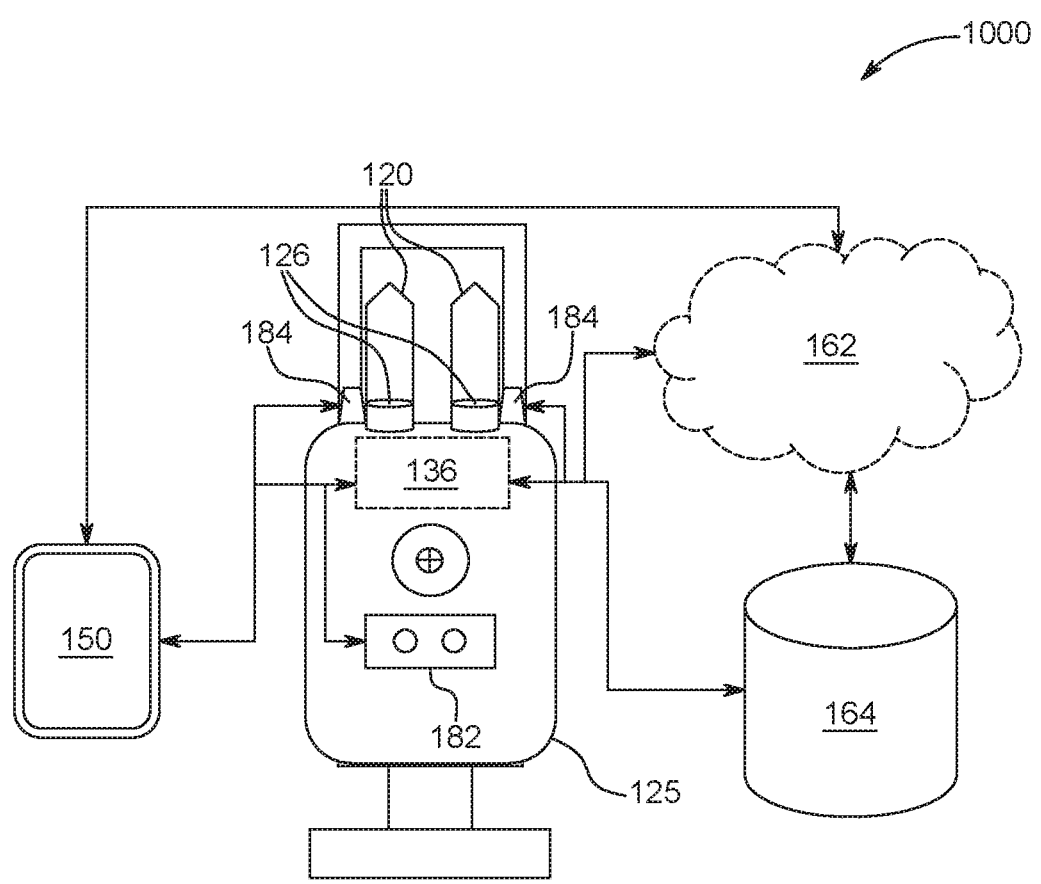
FIG. 11 is a schematic view of an example of a fluid delivery system diagram in accordance with the present disclosure.

FIG. 11 illustrates a system 1000 for controlling a fluid delivery in accordance with a non-limiting example of the present disclosure. In the non-limiting example shown, a fluid control device 136 comprising at least one processor may be formed as part of or connected to a housing 125 and configured or programmed to control an injection and/or fluid delivery in a syringe 120 engaged in a syringe port 126.

In the non-limiting example shown, the fluid control device 136 is in wired and/or wireless communication, as described herein, with a user interface 150 such as a removable touch screen tablet computer or other computer interface, a network 162, a patient records database 164, a plurality of syringe identification sensors 184, and a secondary controller 182. In further non-limiting examples, the user interface 150 may be further configured to be in wired or wireless communication with a medical scanner, an injection protocol database, or other device or system and to allow a user to download, upload, display, and/or manipulate data from the medical scanner, injection protocol database, and/or other systems related to the medical injection procedure.

In the non-limiting example of FIG. 11, the fluid control device 136 may be provided with container identification sensors 184 associated with each fluid interface, such as a syringe port 126 provided in FIG. 11, or containers 26 and 28 and/or drip chambers 1716 of FIG. 2, and in communication with the processor of the fluid control device 136 as well as with the user interface 150. Each container identification sensor 184 may comprise a sensor such as a camera, a radio frequency receiver, an optical label reader, a magnetic sensor, an optical sensor, a mechanical sensor, or any combination thereof, which is configured to detect identifying information about a syringe 120 or other fluid chamber engaged within its corresponding syringe port and communicate this information to the processor of the fluid control device 136 and/or user interface 150. Container identification sensors 184 may receive fill volume data from syringes optically, for example, by tracking the changes in plunger position and/or meniscus level of a fluid in a syringe, or by change in mass. Container identification sensors 184 may transmit this data to the fluid control device 136 or another processor comprising appropriate image recognition software used to identify a change in fill volume without input from a user. The fill volume, and any changes therein, may be displayed on the GUI 5000 of the user interface 150.

In an example according to the present disclosure, data on the liquid-gas interface may be synchronized with the fluid control module 24, the processor 116, or other processor.

Figure 12:
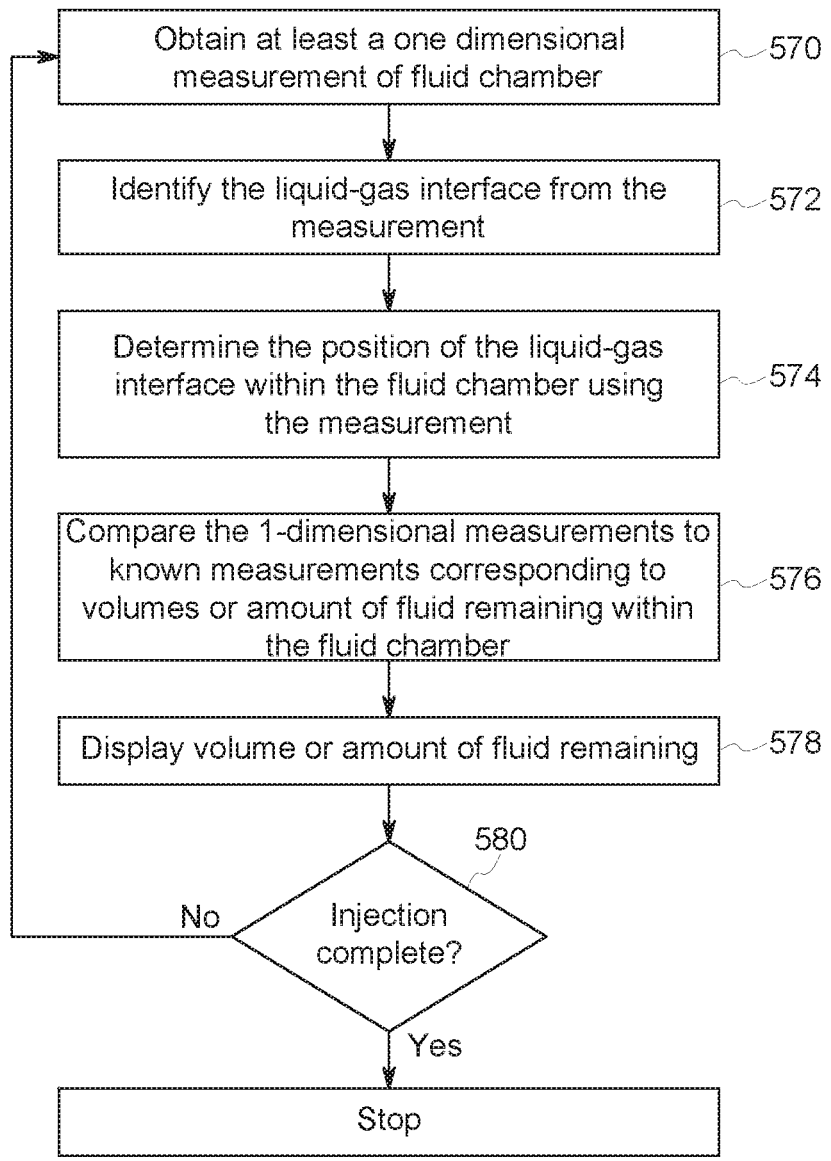
FIG. 12 is a flow chart of a method for determining the volume of fluid remaining within a syringe utilizing image processing techniques in accordance with an aspect of the present disclosure.

In one example, the fluid injector 10 of FIG. 2 may be arranged such that the at least one sensor 3000, 1484 can take a measurement or measurements of the liquid-gas interface in a container 26, 28, and/or drip chamber 1716, respectively. Based on these measurements, the volume, weight, or concentration of contrast or saline remaining within the containers 26, 28 can be determined. Specifically, with reference to FIG. 12, an at least one dimensional measurement of the container 26, 28, is obtained by sensors 3000 at step 570. Then, at step 572, the measurement processing software identifies the liquid-gas interface in the measurement as described herein. Next, at step 574, the measurement processing software determines the position of the liquid-gas interface within the container 26, 28 by determining the change in location of the liquid-gas interface relative to a reference point. In certain embodiments, steps 572 and 574 may be used for example during an optical measurement and may be optional but not necessary for other means of measuring, for example measurements of weight of the fluid using a scale. Once the position of the liquid-gas interface within the container 26, 28 has been determined, this position can be compared to known positions corresponding to a volume or amount of fluid remaining within the containers 26, 28 at step 576. The processor 116 then sends a signal to display the volume or amount of fluid remaining to the display 118 at step 578. The volume or amount remaining may be displayed as a numerical value, or a graphical representation of the container 26, 28 may be displayed that illustrates the real-time volume or amount remaining within the container. Data are taken at a sufficient rate and the display of volume or amount remaining is updated at a sufficient rate until the injection procedure is complete as determined at step 580. In an example according to the present disclosure, imaging or other software on the processor 116, or another processor operatively connected to the fluid injector 10, may automatically stop the injection procedure at step 580. It will be understood that this method may be applied to determining the fluid volume or amount in a drip chamber 1716 with the sensor 1484. It will be further understood that in an example according to the present disclosure, the method described herein may be performed with image data taken of the liquid-gas interface by an optical device such as a camera.

Figure 13:
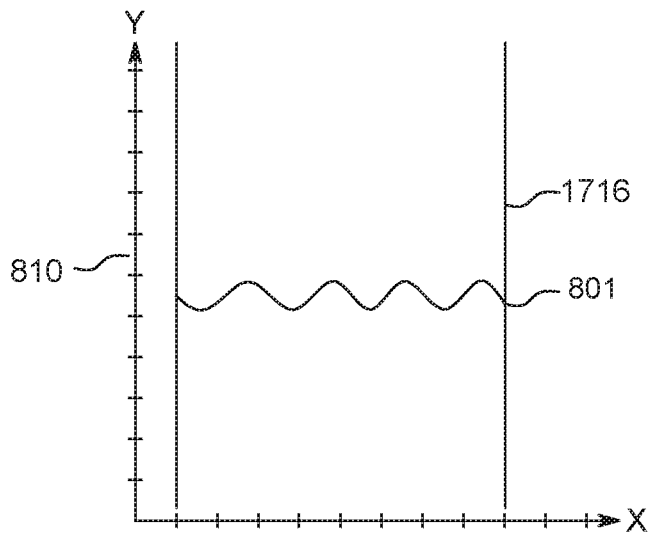
FIG. 13 is a schematic view of an example of a fluid chamber superimposed over a vertical position scale.

FIG. 13 shows a schematic representation of a cross section of a drip chamber 1716 viewed from the perspective of a sensor 1484, with a position measuring scale 801. While this Figure contemplates a drip chamber, it is to be understood that the description herein may apply to determining fluid levels in other fluid chambers, such as bulk containers 26 and 28, with sensors 3000 as well. In an example according to the present disclosure, a position measuring scale 810 may be physically located on the drip chamber 1716, or otherwise physically in view of the sensor 1484. In examples, the measuring scale 810 may be electronically superimposed in a graphical representation 5011, 5012 by imaging software or other software on the processor 116 (see FIG. 10). The sensor 1484 is positioned or otherwise calibrated so that the detected position of the liquid-gas interface 801 corresponds to an actual vertical level of the liquid-gas interface in the liquid chamber. When the liquid-gas interface reaches a predetermined level, as detected by the sensor 1484, an operator may be notified. As shown in FIG. 13, position the measuring scale 810 may be behind, a part of, or imposed over the drip chamber 1716, or other fluid chamber. In an example according to the present disclosure, imaging or other software on the processor 116, or another processor operatively connected to the fluid injector 10, may automatically continue, or stop the injection procedure based on the detected position of the liquid-gas interface 801 with respect to the measuring scale 810.

Figure 14:
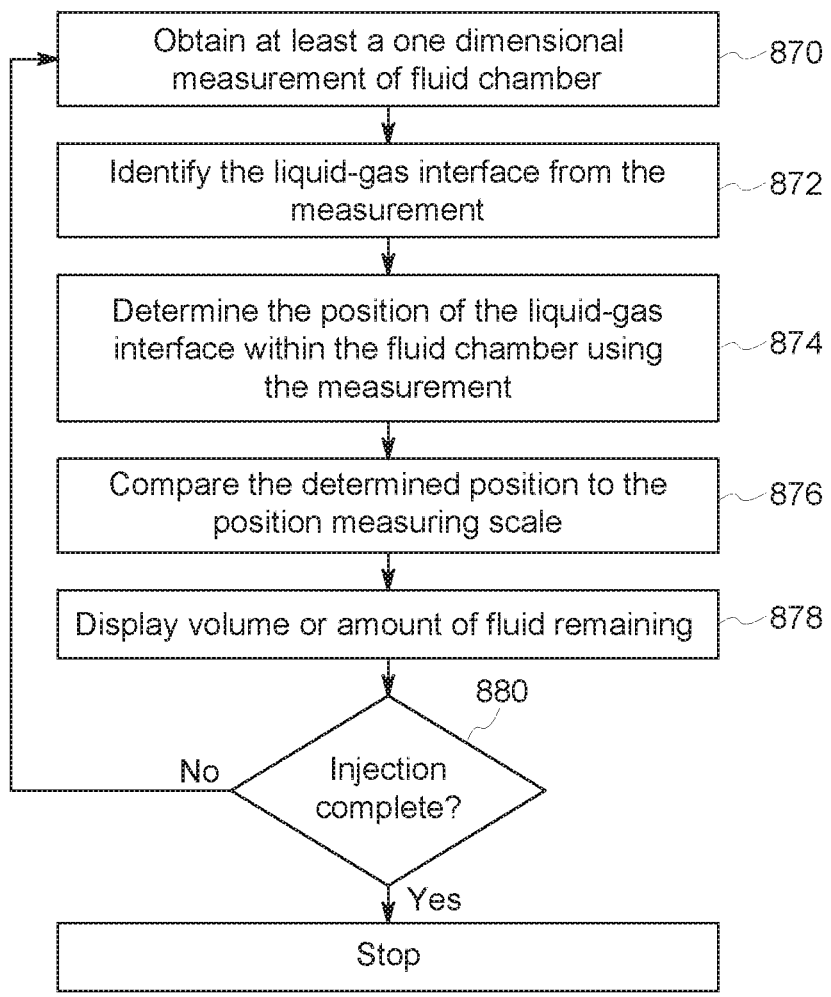
FIG. 14 is a flow chart of a method for determining the volume of fluid remaining within a syringe utilizing image processing techniques in accordance with an aspect of the present disclosure.

With reference to FIG. 14, an at least one dimensional measurement of the bulk fluid container 26, 28, is obtained by sensors 3000 at step 870. Then, at step 872, the measurement processing software identifies the liquid-gas interface in the measurement as discussed herein. Next, at step 874, the measurement processing software determines the position of the liquid-gas interface within the bulk fluid container 26, 28 by determining the position of the liquid-gas interface relative to a level on the measuring scale 810. Once the position of the liquid-gas interface within the container 26, 28 has been determined, this position can be compared to known positions corresponding to a volume or amount of fluid remaining within the containers 26, 28 at step 876. The processor 116 then sends a signal to display the volume or amount remaining to the display 118 at step 878. The volume or amount remaining may be displayed as a numerical value or a graphical representation of the container 26, 28 may be displayed that illustrates the real-time volume or amount remaining within the container. Data may be taken at a sufficient rate and the display of volume remaining is updated at a sufficient rate until the injection procedure is complete as determined at step 880. In an example according to the present disclosure, imaging or other software on the processor 116, or another processor operatively connected to the fluid injector 10, may automatically stop the injection procedure at step 880 based on the detected position of the liquid-gas interface 801. It will be understood that this method may be applied to determining the fluid volume or amount in another fluid chamber, such as a drip chamber 1716 with a sensor 1484. It will be further understood that in an example according to the present disclosure, the method described herein may be performed with image data taken of the liquid-gas interface by an optical device such as a camera.

Various embodiments according to the present disclosure may be characterized by one or more of the following clauses.

Clause 1: A fluid injection system comprises: a fluid injector 10; at least one fluid chamber 14, 26, 28, 1716 configured to contain fluid, the at least one fluid chamber 14, 26, 28, 1716 in fluid communication with the fluid injector 10; one or more sensors 2000, 3000, 1484 positioned relative to the at least one fluid chamber 14, 26, 28, 1716 and configured to detect a position of a liquid-gas interface of the fluid contained in the at least one fluid chamber 14, 26, 28, 1716; at least one processor 116 in communication with the one or more sensors 2000, 3000, 1484 and the fluid injector 10, the at least one processor 116 configured to: determine the position of the liquid-gas interface of the fluid in the at least one fluid chamber 14, 26, 28, 1716; calculate the volume of fluid contained in the at least one fluid chamber 14, 26, 28, 1716 based on the position of the liquid-gas interface of the fluid in the at least one fluid chamber 14, 26, 28, 1716, and at least one of: i) display on a display 118 in communication with the at least one processor 116 the volume of the fluid contained in the at least one fluid chamber 14, 26, 28, 1716; ii) enable the fluid injector 10 to perform an action; iii) inform a user of insufficient volume and allow the user to install a fluid chamber 14, 26, 28, 1716 having sufficient volume; iv) inform the user of insufficient volume and allow the user to continue with a system-adjusted volume or a user-adjusted volume; and v) disable the fluid injector 10 from performing the action.

Clause 2: The fluid injection system of clause 1, wherein the at least one fluid chamber 14, 26, 28, 1716 comprises a contrast media container 26 and a saline container 28.

Clause 3: The fluid injection system of clause 2, wherein the fluid injector 10 comprises a pump 22 and is in fluid communication with a fluid path set 17; wherein the at least one fluid chamber 14, 26, 28, 1716 further comprises at least one drip chamber 1716 in fluid communication with the fluid injector 10 and at least one of the contrast media container 26 and the saline container 28; and wherein at least one of the one or more sensors 1484 is positioned relative to the at least one drip chamber 1716 and configured to detect the position of a liquid-gas interface of a fluid contained in the at least one drip chamber 1716.

Clause 4: The fluid injection system of clause 3, wherein the pump 22 comprises a peristaltic pump 22.

Clause 5: The fluid injection system of any of clauses 1 to 4, wherein the one or more sensors 2000, 3000, 1484 comprises an optical sensor.

Clause 6: The fluid injection system of any of clauses 1 to 5, wherein the display 118 comprises a graphical user interface 5000, and wherein the position of the liquid-gas interface of the fluid in the at least one fluid chamber 14, 26, 28, 1716 is displayed on the display graphical user interface 5000.

Clause 7: The fluid injection system of any of clauses 1 to 6, wherein the one or more sensors 2000, 3000, 1484 comprise an ultrasonic sensor.

Clause 8: The fluid injection system of any of clauses 1 to 7, wherein the one or more sensors 2000, 3000, 1484 comprise an array of sensors.

Clause 9: The fluid-injection system of any of clauses 1 to 8, which further comprises an actuator configured to actuate the one or more sensors 2000, 3000, 1484; wherein the one or more sensors 2000, 3000, 1484 are actuated to move in response to the position of the liquid-gas interface of the fluid in the at least one fluid chamber 14, 26, 28, 1716.

Clause 10: A method for determining the volume of fluid in at least one fluid chamber 14, 26, 28, 1716 of a fluid injection system which comprises a fluid injector 10, the method comprises the steps of: positioning one or more sensors 2000, 3000, 1484 relative to the at least one fluid chamber 14, 26, 28, 1716, wherein the one or more sensors 2000, 3000, 1484 are in communication with at least one processor 116 in communication with the fluid injector 10; detecting with the one or more sensors 2000, 3000, 1484 a position of a liquid-gas interface of the fluid contained in the at least one fluid chamber 14, 26, 28, 1716; taking position data of the liquid-gas interface of the fluid contained in the at least one fluid chamber 14, 26, 28, 1716 with at least one of the one or more sensors 2000, 3000, 1484; determining the position of the liquid-gas interface of the fluid in the at least one fluid chamber 14, 26, 28, 1716 from the position data; calculating the volume of fluid contained in the at least one fluid chamber 14, 26, 28, 1716 based on the position of the liquid-gas interface of the fluid in the at least one fluid chamber 14, 26, 28, 1716; and at least one of: i) displaying on a display 118 in communication with the at least one processor 116 the volume of the fluid contained in the at least one fluid chamber 14, 26, 28, 1716; ii) enabling the fluid injector 10 to perform an action; iii) informing a user of an insufficient volume and allowing the user to install a fluid container 14, 26, 28, 1716 having a sufficient volume; iv) informing the user of the insufficient volume and allowing the user to continue with a system-adjusted volume or a user-adjusted volume; and v) disabling the fluid injector 10 from performing the action.

Clause 11: The method according to clause 10, wherein the steps of enabling the fluid injector 10 to perform the function, and disabling the fluid injector 10 from performing the action, are automatically completed by the at least one processor 116.

Clause 12: The method according to any of clauses 10 to 11, wherein the one or more sensors 2000, 3000, 1484 comprise a one-dimensional optical device Clause 13: The method according to any of clauses 10 to 12, which further comprises the steps of: determining the volume of fluid contained in the at least one fluid chamber 14, 26, 28, 1716 by comparing the position data with known positions corresponding to known volumes of fluid.

Clause 14: The method according to any of clauses 10 to 12, which further comprises the steps of: positioning a position measuring scale 810 within a field of detection of the one or more sensors; comparing the position data with the positioning measuring scale; and determining the volume of fluid contained in the at least one fluid chamber 14, 26, 28, 1716 based on a relative position of the liquid-gas interface and a value indicated by the measuring scale 810.

Clause 15: The method according to any of clauses 10 to 14, wherein the at least one fluid chamber 14, 26, 28, 1716 comprises a contrast media container 26 and saline container 28.

Clause 16: The method according to clause 15, wherein the fluid injector 10 comprises a pump 22, and is in fluid communication with a fluid path set 17; wherein the at least one fluid chamber 14, 26, 28, 1716 further comprises at least one drip chamber 1716 in fluid communication with the fluid injector 10 and at least one of the contrast media container 26 and the saline container 28; and wherein at least one of the one or more sensors 1484 is positioned relative to the at least one drip chamber 1716 and configured to detect the position of the liquid-gas interface of the fluid contained in the at least one drip chamber 1716.

Clause 17: The method according to clause 16, wherein the pump 22 comprises a peristaltic pump 22.

Clause 18: The method according to any of clauses 10 to 17, wherein the display 118 comprises a graphical user interface 5000, and wherein the position of the liquid-gas interface of the fluid in the at least one fluid chamber 14, 26, 28, 1716 is displayed on the graphical user interface 5000.

Clause 19: The method according to any of clauses 10 to 18, wherein the one or more sensors 2000, 3000, 1484 comprise an ultrasonic sensor.

Clause 20: The method according to any of clauses 10 to 19, wherein the fluid injector 10 comprises an actuator configured to actuate at least one of the one or more sensors 2000, 3000, 1484, and further comprises the step of: actuating the one or more sensors 2000, 3000, 1484 to move in response to the position of the liquid-gas interface of the fluid in the at least one fluid chamber 14, 26, 28, 1716.

Clause 21: The method according to any of clauses 10 to 11, wherein the one or more sensors 2000, 3000, 1484 comprise an optical device; and the position data of the liquid-gas interface of fluid contained in the at least one fluid chamber 14, 26, 28, 1716 comprise image data.

Although the disclosure has been described in detail for the purpose of illustration based on what is currently considered to be the most practical and preferred embodiments, it is to be understood that such detail is solely for that purpose and that the disclosure is not limited to the disclosed embodiments, but, on the contrary, is intended to cover modifications and equivalent arrangements. For example, it is to be understood that the present disclosure contemplates that, to the extent possible, one or more features of any embodiment can be combined with one or more features of any other embodiment.

We claim:

1. A fluid injection system comprising:
   a fluid injector;
   at least one fluid chamber configured to contain fluid, the at least one fluid chamber in fluid communication with the fluid injector;
   one or more electromagnetic radiation or ultrasonic sensors positioned relative to the at least one fluid chamber and configured to detect a position of a liquid-gas interface of the fluid contained in the at least one fluid chamber by dithering a field of the one or more electromagnetic or ultrasonic sensors; and
   at least one processor in communication with the one or more electromagnetic radiation or ultrasonic sensors and the fluid injector, the at least one processor configured to:
   determine the position of the liquid-gas interface of the fluid in the at least one fluid chamber;
   calculate the volume of fluid contained in the at least one fluid chamber based on the position of the liquid-gas interface of the fluid in the at least one fluid chamber, and
   at least one of:
   display on a display in communication with the at least one processor, the volume of the fluid contained in the at least one fluid chamber;

enable the fluid injector to perform an action;
inform a user of an insufficient volume of fluid to perform the action and allow the user to install a fluid container having a sufficient volume of fluid;
inform the user of the insufficient volume of fluid and allow the user to continue with a system-adjusted volume of fluid or a user-adjusted volume of fluid; and
disable the fluid injector from performing the action.

2. The fluid injection system of claim 1, wherein the at least one fluid chamber comprises a contrast media container and a saline container.

3. The fluid injection system of claim 2,
wherein the fluid injector comprises a pump and is in fluid communication with a fluid path set;
wherein the at least one fluid chamber further comprises at least one drip chamber in fluid communication with the fluid injector and at least one of the contrast media container and the saline container; and
wherein at least one of the one or more electromagnetic radiation or ultrasonic sensors is positioned relative to the at least one drip chamber and configured to detect a position of a liquid-gas interface of a fluid contained in the at least one drip chamber.

4. The fluid injection system of claim 3, wherein the pump comprises a peristaltic pump.

5. The fluid injection system of claim 1, wherein the one or more electromagnetic radiation or ultrasonic sensors comprise an optical sensor.

6. The fluid injection system of claim 1, wherein the display comprises a graphical user interface, and
wherein the position of the liquid-gas interface of the fluid in the at least one fluid chamber is displayed on the graphical user interface.

7. The fluid-injection system of claim 1, wherein the one or more electromagnetic radiation or ultrasonic sensors comprise an ultrasonic sensor.

8. The fluid-injection system of claim 1, wherein the one or more electromagnetic radiation or ultrasonic sensors comprise an array of electromagnetic radiation or ultrasonic sensors.

9. The fluid-injection system of claim 1, further comprising an actuator configured to actuate the one or more electromagnetic radiation or ultrasonic sensors;
wherein the one or more electromagnetic radiation or ultrasonic sensors are actuated to move in response to the position of the liquid-gas interface of the fluid in the at least one fluid chamber.

10. A method for determining a volume of fluid in at least one fluid chamber of a fluid injection system comprising a fluid injector, the method comprising:
positioning one or more electromagnetic radiation or ultrasonic sensors relative to the at least one fluid chamber, wherein the one or more electromagnetic radiation or ultrasonic sensors are in communication with at least one processor in communication with the fluid injector;
dithering a field of detection of the one or more electromagnetic radiation or ultrasonic sensors to detect a position of a liquid-gas interface of the fluid contained in the at least one fluid chamber;
taking position data of the liquid-gas interface of the fluid contained in the at least one fluid chamber with at least one of the one or more electromagnetic radiation or ultrasonic sensors;
determining the position of the liquid-gas interface of the fluid in the at least one fluid chamber from the position data;
calculating the volume of fluid contained in the at least one fluid chamber based on the position of the liquid-gas interface of the fluid in the at least one fluid chamber; and
at least one of:
displaying on a display in communication with the at least one processor, the volume of the fluid contained in the at least one fluid chamber;
enabling the fluid injector to perform an action;
informing a user of an insufficient volume of fluid to perform the action and allowing the user to install a fluid container having a sufficient volume of fluid;
informing the user of the insufficient volume of fluid and allowing the user to continue with a system-adjusted volume of fluid or a user-adjusted volume of fluid; and
disabling the fluid injector from performing the action.

11. The method according to claim 10, wherein enabling the fluid injector to perform the action, and disabling the fluid injector from performing the action, are automatically completed by the at least one processor.

12. The method according to claim 10, wherein the one or more electromagnetic radiation or ultrasonic sensors comprise an optical sensor.

13. The method according to claim 10, further comprising:
determining the volume of fluid contained in the at least one fluid chamber by comparing the position data with known positions corresponding to known volumes of fluid.

14. The method according to claim 10, further comprising:
positioning a position measuring scale within a field of detection of the one or more electromagnetic radiation or ultrasonic sensors;
comparing the position data with the position measuring scale; and
determining the volume of fluid contained in the at least one fluid chamber based on a relative position of the liquid-gas interface and a value indicated by the position measuring scale.

15. The method according to claim 10, wherein the at least one fluid chamber comprises a contrast media container and a saline container.

16. The method according to claim 15, wherein the fluid injector comprises a pump, and is in fluid communication with a fluid path set;
wherein the at least one fluid chamber further comprises at least one drip chamber in fluid communication with the fluid injector and at least one of the contrast media container and the saline container; and
wherein at least one of the one or more electromagnetic radiation or ultrasonic sensors is positioned relative to the at least one drip chamber and configured to detect a position of a liquid-gas interface of the fluid contained in the at least one drip chamber.

17. The method according to claim 16, wherein the pump comprises a peristaltic pump.

18. The method according to claim 10, wherein the display comprises a graphical user interface, and
wherein the position of the liquid-gas interface of the fluid in the at least one fluid chamber is displayed on the graphical user interface.

19. The method according to claim 10, wherein the one or more electromagnetic radiation or ultrasonic sensors comprise an ultrasonic sensor.

20. The method according to claim 10, wherein the fluid injector comprises an actuator configured to actuate at least one of the one or more electromagnetic radiation or ultrasonic sensors, the method further comprising:
- actuating the one or more electromagnetic radiation or ultrasonic sensors to move in response to the position of the liquid-gas interface of the fluid in the at least one fluid chamber.

\* \* \* \* \*